(12) United States Patent
Dokter et al.

(10) Patent No.: US 11,382,982 B2
(45) Date of Patent: Jul. 12, 2022

(54) DUOCARMYCIN ADCS SHOWING IMPROVED IN VIVO ANTITUMOR ACTIVITY

(71) Applicant: Byondis B.V., Nijmegen (NL)

(72) Inventors: Willem Dokter, Nijmegen (NL); Peter Johannes Goedings, Nijmegen (NL); Gijsbertus Franciscus Maria Verheijden, Nijmegen (NL); Patrick Henry Beusker, Nijmegen (NL)

(73) Assignee: Byondis B.V., Nijmegen (NL)

( * ) Notice: Subject to any disclaimer, the term of this patent is extended or adjusted under 35 U.S.C. 154(b) by 225 days.

(21) Appl. No.: 16/456,177

(22) Filed: Jun. 28, 2019

(65) Prior Publication Data

US 2019/0314513 A1 Oct. 17, 2019

Related U.S. Application Data

(60) Continuation of application No. 15/798,695, filed on Oct. 31, 2017, now Pat. No. 10,603,387, which is a (Continued)

(30) Foreign Application Priority Data

Jan. 10, 2014 (EP) .................................... 14150791
Oct. 10, 2014 (EP) .................................... 14188450

(51) Int. Cl.
*A61K 47/60* (2017.01)
*A61K 47/68* (2017.01)
(Continued)

(52) U.S. Cl.
CPC ................ *A61K 47/60* (2017.08); *A61K 9/19* (2013.01); *A61K 45/06* (2013.01);
(Continued)

(58) Field of Classification Search
None
See application file for complete search history.

(56) References Cited

U.S. PATENT DOCUMENTS 5,475,092 A 12/1995 Chari et al.
5,502,068 A 3/1996 Lown et al.
(Continued)

FOREIGN PATENT DOCUMENTS

EP 0 263 526 A1 4/1988
EP 0 154 445 B1 5/1989
(Continued)

OTHER PUBLICATIONS

Persson et al. ("Persson", Cancer Res., 2007, 67, 326-331) (Year: 2007).*
(Continued)

*Primary Examiner* — Karl J Puttlitz
(74) *Attorney, Agent, or Firm* — Buscher Patent PLLC

(57) ABSTRACT

The present invention relates to duocarmycin-containing antibody-drug conjugates (ADCs) for use in the treatment of human solid tumours and haematological malignancies expressing HER2, in particular breast cancer, gastric cancer, bladder cancer, ovarian cancer, lung cancer, prostate cancer, pancreatic cancer, colorectal cancer, head and neck squamous cell cancer or osteosarcoma, and acute lymphoblastic leukaemia. In particular, the present invention relates to duocarmycin-containing ADCs for use in the treatment of human solid tumours with HER2 IHC 2+ or 1+ and HER2 FISH negative tissue status. Advantageously, the present invention relates to duocarmycin-containing ADCs for use in the treatment of triple negative breast cancer (TNBC).

10 Claims, 12 Drawing Sheets

Related U.S. Application Data division of application No. 15/216,407, filed on Jul. 21, 2016, now abandoned, which is a division of application No. 14/859,201, filed on Sep. 18, 2015, now Pat. No. 9,421,278, which is a continuation of application No. PCT/EP2015/050350, filed on Jan. 9, 2015.

(51) Int. Cl.
*A61K 45/06* (2006.01)
*C07K 16/40* (2006.01)
*A61K 9/19* (2006.01)
*C07K 16/32* (2006.01)
*A61K 39/00* (2006.01)

(52) U.S. Cl.
CPC ...... *A61K 47/6801* (2017.08); *A61K 47/6803* (2017.08); *A61K 47/6809* (2017.08); *A61K 47/6849* (2017.08); *A61K 47/6851* (2017.08); *A61K 47/6855* (2017.08); *A61K 47/6871* (2017.08); *A61K 47/6889* (2017.08); *C07K 16/32* (2013.01); *C07K 16/40* (2013.01); *A61K 2039/505* (2013.01); *C07K 2317/24* (2013.01); *C07K 2317/76* (2013.01)

(56) References Cited

U.S. PATENT DOCUMENTS

| | | |
|---|---|---|
| 5,579,350 A | 11/1996 | Furukawa et al. |
| 5,662,911 A | 9/1997 | Huber et al. |
| 5,739,350 A | 4/1998 | Kelly et al. |
| 7,064,117 B2 | 6/2006 | Denny et al. |
| 7,705,045 B2 | 4/2010 | De Groot et al. |
| 7,718,688 B2 | 5/2010 | Denny et al. |
| 8,012,978 B2 | 9/2011 | Zhao et al. |
| 8,680,293 B2 | 3/2014 | Beusker et al. |
| 8,889,868 B2 | 11/2014 | Beusker et al. |
| 9,421,278 B2 | 8/2016 | Dokter et al. |
| 9,427,480 B2 | 8/2016 | Santin et al. |
| 9,815,784 B2 | 11/2017 | Beusker et al. |
| 9,890,159 B2 | 2/2018 | Huijbregts et al. |
| 9,901,567 B2 | 2/2018 | Beusker et al. |
| 2003/0073731 A1 | 4/2003 | Lee |
| 2004/0033962 A1 | 2/2004 | Tietze et al. |
| 2004/0120958 A1 | 6/2004 | Bander et al. |
| 2005/0014700 A1 | 1/2005 | Boger |
| 2006/0116422 A1 | 6/2006 | De Groot et al. |
| 2006/0233794 A1 | 10/2006 | Law et al. |
| 2009/0010945 A1 | 1/2009 | Alley |
| 2009/0111805 A1 | 4/2009 | Morris et al. |
| 2009/0162372 A1 | 6/2009 | King et al. |
| 2012/0214864 A1 | 8/2012 | Richer |
| 2013/0095172 A1 | 4/2013 | Alavattam |
| 2013/0224227 A1 | 8/2013 | Beusker et al. |
| 2015/0216844 A1 | 8/2015 | Beusker et al. |
| 2016/0052880 A1 | 2/2016 | Beusker et al. |
| 2016/0324979 A1 | 11/2016 | De Roo et al. |
| 2017/0007717 A1 | 1/2017 | Santin et al. |
| 2017/0080103 A1 | 3/2017 | Ariaans et al. |
| 2017/0320965 A1 | 11/2017 | Egging et al. |

FOREIGN PATENT DOCUMENTS

| | | |
|---|---|---|
| EP | 0 656 360 A1 | 6/1995 |
| EP | 0 702 014 A1 | 3/1996 |
| EP | 0 359 454 B1 | 12/2000 |
| EP | 2 380 909 A1 | 10/2011 |
| JP | H 06-56697 A | 3/1994 |
| JP | H 11-500427 A | 1/1999 |
| JP | 2000-511893 A | 9/2000 |
| JP | 2004-518678 A | 6/2004 |
| JP | 2005-532287 A | 10/2005 |
| JP | 2008-517905 A | 5/2008 |
| JP | 2008-531542 A | 8/2008 |
| JP | 2009-529030 A | 8/2009 |
| WO | WO 94/24304 A1 | 10/1994 |
| WO | WO 96/23497 A1 | 8/1996 |
| WO | WO 97/44000 A2 | 11/1997 |
| WO | WO 98/11101 A2 | 3/1998 |
| WO | WO 98/25900 A1 | 6/1998 |
| WO | WO 99/31120 A1 | 6/1999 |
| WO | WO 01/83448 A2 | 11/2001 |
| WO | WO 02/067930 A1 | 9/2002 |
| WO | WO 02/096910 A1 | 12/2002 |
| WO | WO 03/026577 A2 | 4/2003 |
| WO | WO 03/086318 A2 | 10/2003 |
| WO | WO 03/097635 A1 | 11/2003 |
| WO | WO 2004/032828 A2 | 4/2004 |
| WO | WO 2004/069159 A2 | 8/2004 |
| WO | WO 2004/069201 A2 | 8/2004 |
| WO | WO 2004/101767 A2 | 11/2004 |
| WO | WO 2005/032594 A2 | 4/2005 |
| WO | WO 2005/084390 A2 | 9/2005 |
| WO | WO 2005/112919 A2 | 12/2005 |
| WO | WO 2006/034488 A2 | 3/2006 |
| WO | WO 2006/037052 A2 | 4/2006 |
| WO | WO 2007/038658 A2 | 4/2007 |
| WO | WO 2007/051081 A1 | 5/2007 |
| WO | WO 2007/089149 A2 | 8/2007 |
| WO | WO 2008/063378 A2 | 5/2008 |
| WO | WO 2008/074004 A2 | 6/2008 |
| WO | WO 2008/103693 A2 | 8/2008 |
| WO | WO 2009/017394 A1 | 2/2009 |
| WO | WO 2009/064908 A1 | 5/2009 |
| WO | WO 2009/064913 A1 | 5/2009 |
| WO | WO 2010/027280 A1 | 3/2010 |
| WO | WO 2010/033733 A1 | 3/2010 |
| WO | WO 2010/062171 A2 | 6/2010 |
| WO | WO 2011/133039 A2 | 10/2011 |
| WO | WO 2011133039 A2 | 10/2011 |
| WO | WO 2012/143523 A1 | 10/2012 |
| WO | WO 2013/049410 A1 | 4/2013 |
| WO | WO 2013/093809 A1 | 6/2013 |
| WO | WO2013/121175 A1 | 8/2013 |
| WO | WO 2015/104359 A2 | 7/2015 |
| WO | WO 2015/104373 A2 | 7/2015 |
| WO | WO 2015/185142 A1 | 12/2015 |
| WO | WO 2016/046173 A1 | 3/2016 |
| WO | WO 2017/009255 A1 | 1/2017 |

OTHER PUBLICATIONS

Siva The lancet Oncology, 8(7) 2007, 576 (Year: 2007).*
Simon Langdon ("Langdon", J. Mol. Biomarkers & Diagnosis, 2012, 3, 1-2) (Year: 2012).
Hussain et al. ("Hussain" J. Clin. Onc., 2007, 25, pp. 2218-2224.
English language translation of WO 98/25900(cited as document FP2 on accompanying form PTO/SB/08A), Google translate, Apr. 30, 2013.
Amsellem-Ouazana, D., et al., "Management of Primary Resistance to Gemcitabine and Cisplatin (G-C) Chemotherapy in Metastatic Bladder Cancer With Her2 Over-Expression," *Ann. Oncol.*, 15(3): 538, Kluwer Academic Publishers, United States (2004).
Bartlett, J.M.S., et al., "Type I Receptor Tyrosine Kinases Are Associated With Hormone Escape in Prostate Cancer," *J Pathol.*, 205: 522-529, John Wiley and Sons Ltd., England (2005).
Beckhardt, R.N., et al., "HER-2/neu Oncogene Characterization in Head and Neck Squamous Cell Carcinoma," *Arch. Otolaryngol. Head Neck Surg.* 121:1265-1270, American Medical Association, United States (1995).
Berchuck, A., et al., "Overexpression of HER-2/neu Is Associated with Poor Survival in Advanced Epithelial Ovarian Cancer," *Cancer Res.*, 50: 4087-4091, American Association for Cancer Research, United States (1990).
Bertotti, A., et al., "A Molecularly Annotated Platform of Patient-Derived Xenografts ("Xenopatients") Identifies HER2 as an Effective Therapeutic Target in Cetuximab-Resistant Colorectal Cancer," *Cancer Discov.* 1(6): 508-523, American Association for Cancer Research, United States (2011).

(56) References Cited

OTHER PUBLICATIONS

Boger, D.L. and Johnson, D.S., "CC-1065 and the Duocarmycins: Unraveling the Keys to a New Class of Naturally Derived DNA Alkylating Agents," *Proc. Natl. Acad. Sci.* 92(9): 3642-3649, American Association for the Advancement of Science, United States (1995).

Boger, D.L., et al. "Synthesis and Properties of Substituted CBI Analogs of CC-1065 and the Duocarmycins Incorporating the 7-Methoxy-1,2,9,9a-tetrahydrocyclopropa[c]benz[e]indol-4-one (MCBI) Alkylation Subunit: Magnitude of Electronic Effects on the Functional Reactivity," *Journal of Organic Chemistry 8*;61(5):1710-1729, American Chemical Society, United States (1996).

Braga, D., et al., "Crystal Polymorphism and Multiple Crystal Forms" *Struct. Bond.*, 132: 25-50 Springer-Verlag, Germany (2009).

Burris, H. and Storniolo, AM., "Assessing Clinical Benefit in the Treatment of Pancreas Cancer: Gemcitabine Compared to 5-Fluorouracil," *Eur. J Cancer* 33(Suppl. J):S18-S22, Elsevier Science Ltd., England (1997).

Cai, C., et al., "Androgen Receptor Expression in Prostate Cancer Cells Is Suppressed by Activation of Epidermal Growth Factor Receptor and ErbB2," *Cancer Res.*, 69(12): 5202-5209, American Association for Cancer Research, United States (2009).

Calikusu, Z., et al., "The Effect Of HER2 Expression on Cisplatin-Based Chemotherapy in Advanced Non-Small Cell Lung Cancer Patients," *J. Exp. Clin. Cancer Res.*, 28(1):97, BioMed Central Ltd., England (2009).

Chakravarti, A., et al., "Expression of the epidermal growth factor receptor and Her-2 are predictors of favorable outcome and reduced complete response rates, respectively, in patients with muscle-invading bladder cancers treated by concurrent radiation and cisplatin-based chemotherapy: A report from the Radiation Therapy Oncology Group," *Int. J. Radiation Oncology Biol. Phys.*, 62(2): 309-317, Elsevier, The Netherlands (2005).

Chen, L., et al., "Dual EGFR/HER2 Inhibition Sensitizes Prostate Cancer Cells to Androgen Withdrawal by Suppressing ErbB3," *Clin. Cancer Res.*, 17(19): 6218-28, American Association for Cancer Research, United States (2011).

Chevallier, et al., "Trastuzumab for Treatment of Refractory/ Relapsed HER2-Positive Adult B-ALL: Results of a Phase 2 GRAALL Study," *Blood*, 119(11): 2474-7, The American Society of Hematology, United States (2012).

Clark, J., et al., "Phase II Trial Of 5-Fluororuacil (5-FU), Leucovorin (LV), Oxaliplatin (Ox), and Trastuzamab (T) for Patients With Metastatic Colorectal Cancer (CRC) Refractory to Initial Therapy," *Proc. Am. Soc. Clin. Oncol.* 22:891-abstr 3584, American Society of Clinical Oncology, United States (2003).

Conroy, T., et al., "FOLFIRINOX Versus Gemcitabine for Metastatic Pancreatic Cancer," *N. Engl. J. Med.* 364(19): 1817-25, Massachusetts Medical Society, United States (2011).

Dokter, W., et al., "Abstract 4329: Novel Her2 Targeting Antibody-Drug Conjugates Based on DNA-Interacting Duocarmycin and an Unique Linker Technology With Great Potential in Breast Cancer and NSCLC," Proceedings of the 104th Annual Meeting of the American Association for Cancer Research; Apr. 6-10, 2013; *Cancer Res* 73(8Suppl):Abstract nr 4329, AACR, United States (2013).

Dokter, W., et al., "Preclinical Profile of the HER2-Targeting ADC SYD983/SYD985: Introduction of a New Duocarmycin-Based Linker-Drug Platform" (Supplemental Data Included) *Molecular Cancer Therapeutics I* 3(11):2618-2629, American Association of Cancer Research, United States (Sep. 2014).

Ebb, D., et al., "Phase II Trial of Trastuzumab in Combination With Cytotoxic Chemotherapy for Treatment of Metastatic Osteosarcoma With Human Epidermal Growth Factor Receptor 2 Overexpression: A Report From the Children's Oncology Group," *J. Clin. Oncol.* 30(20): 2545-2551, American Society of Clinical Oncology, United States (2012).

English, D.P., et al., "T-DM1, A Novel Antibody-Drug Conjugate, Is Highly Effective Against Primary HER2 Overexpressing Uterine Serous Carcinoma In Vitro and In Vivo," *Cancer Medicine* 3(5): 1256-1265, John Wiley and Sons, United States (Jun. 2014).

Extended European Search Report for EP Application No. EP 14 15 0791, European Patent Office, Germany, dated Jun. 30, 2014, 17 pages.

Fiebig et al., "Comparison of Tumor Response in Nude Mice and in the Patients," *Behring Inst. Mitt.* 74: 343-352, Nature Publishing Group, England (1984).

Fiebig, H.H., et al., "Gene Signatures Developed From Patient Tumor Explants Grown [n Nude Mice to Predict Tumor Response to 11 Cytotoxic Drugs," *Cancer Genomics & Proteomics 4*: 197-2 I 0, International Institute of Anticancer Research, Greece (1997).

Fleming et al.,"Phase II Trial of Trastuzumab in Women with Advanced or Recurrent, HER2-Positive Endometrial Carcinoma: a Gynecologic Oncology Group Study," *Gynecol. Oncol. I* 16(1): 15-20, Elsevier Inc., The Netherlands (2010).

Flygare, J.A., et al., "Antibody-Drug Conjugates for the Treatment of Cancer," *Chemical Biology & Drug Design*, 81(1):113-121, John Wiley & Sons A/S, United States (Jan. 2013).

Gaborit, N., et al., "Time-Resolved Fluorescence Resonance Energy Transfer (TR-FRET) to Analyze the Disruption of EGFR/HER2 Dimers: A New Method to Evaluate the Efficiency of Targeted Therapy Using Monoclonal Antibodies," *J Biol. Chem.*, 286(13): 11337-11345, American Society for Biochemistry and Molecular Biology, United States (2011).

Garg, K. and Soslow, R.A., "Endometrial Carcinoma in Women Aged 40 Years and Younger," *Arch. Pathol. Lab. Med.*, I 38: 335-342, College of American Pathologists, United States (Mar. 2014).

Gorlick, R., et al., "Expression of HER2/erbB-2 Correlates With Survival in Osteosarcoma," *J Clin. Oncol.* 17(9):2781-8, American Society of Clinical Oncology, United States (1999).

Hidalgo, et al., "A Pilot Clinical Study of Treatment Guided by Personalized Tumorgrafts in Patients With Advanced Cancer," *Mo/. Cancer Ther.* 10(8):1311-1316, American Association for Cancer Research, United States (2011).

Hsu, F.-N., et al., "The Significance Of Her2 on Androgen Receptor Protein Stability in the Transition of Androgen Requirement in Prostate Cancer Cells," *Am. J Physiol. Endocrinol. Metab.*, 300:E902-E908, American Physiological Society, United States (2011).

Hussain, M.H.A., et al., "Trastuzumab, Paclitaxel, Carboplatin, and Gemcitabine in Advanced Human Epidermal Growth Factor Receptor-2/neu-Positive Urothelial Carcinoma: Results of a Multicenter Phase II National Cancer Institute Trial," *J. Clin. Oncol.*, 25(16): 2218-24, American Society of Clinical Oncology, United States (2007).

International Search Report and Written Opinion for International Application No. PCT/EP2015/050332, European Patent Office, Netherlands, dated Jul. 20, 2015, 15 Pages.

International Search Report and Written Opinion for International Application No. PCT/EP2015/050350, European Patent Office, Netherlands, dated Jul. 6, 2015, 14 Pages.

Irwin, M.E., et al., "Small Molecule ErbB Inhibitors Decrease Proliferative Signaling and Promote Apoptosis in Philadelphia Chromosome-Positive Acute Lymphoblastic Leukemia," *PLoS One*, 8(8): e70608, Public Library of Science, United States (2013).

Jewell, E. et al., "Use of Trastuzumab in the Treatment of Metastatic Endometrial Cancer" *Int. J. Gynecol. Cancer* 16: 1370-1373, Lippincott Williams & Wilkins, United States (2006).

Kazane, S. A., et al., "Site-Specific DNA-Antibody Conjugates for Specific and Sensitive Immuno-PCR," *Proceedings of the National Academy of Sciences*, 109(10):3731-3736, United States National Academy of Sciences, United States (2012).

Kelly, R.K., et al., "An Antibody-Cytotoxic Conjugate, BIIB015, Is a New Targeted Therapy for Cripto Positive Tumours," *European Journal of Cancer* 47(! 1):1736-1746, Pergamon Press, England (2011).

Kutty, R.V., et al., "Cetuximab Conjugated Vitamine E TPGS Micelles for Targeted Delivery of Docetaxel for Treatment of Triple Negative Breast Cancers," *Biomaterials*, 34(38): IO160-10171, Elsevier Science, The Netherlands (2013).

Langdon, S.P., et al., "Pertuzumab for the treatment of ovarian cancer," *Expert Opin. Biol. Ther.* 10(7): 1113-1120, Informa UK Ltd., England (2010).

Larbouret, C., et al., "In Pancreatic Carcinoma, Dual EGFR/HER2 Targeting with Cetuximab/Trastuzumab Is More Effective than

(56) References Cited

OTHER PUBLICATIONS

Treatment with Trastuzumab/Erlotinib or Lapatinib Alone: Implication of Receptors' Down-regulation and Dimers' Disruption," *Neoplasia* 14(2): 121-130, Elsevier, The Netherlands (2012).

Makhija, S., et al., "Clinical Activity of Gemcitabine Plus Pertuzumab in Platinum-Resistant Ovarian Cancer, Fallopian Tube Cancer, or Primary Peritoneal Cancer," *J. Clin. Oncol.*, 28(7): 1215-1223, American Society of Clinical Oncology, United States.

Mantia-Smaldone, G.M., et al., "Targeted treatment of recurrent platinum-resistant ovarian cancer: current and emerging therapies," *Cancer Management Res.* 3: 25-38, Dove Medical Press Ltd., England (2011).

Mazieres, J., et al., "Lung Cancer That Harbors an HER2 Mutation: Epidemiologic Characteristics and Therapeutic Perspectives," *J. Clin. Oncol.*, 31(16): 1997-2003, American Society of Clinical Oncology, United States (2013).

Meden, H. and Kuhn, W., "Overexpression of the oncogene c-erbB-2 (HER2/neu) in ovarian cancer: a new prognostic factor," *Eur. J. Obstet. & Gynecol. Reprod. Biol.*, 71: 173-179, Elsevier, The Netherlands (1997).

Minner, S., et al., "Low level HER2 Overexpression Is Associated With Rapid Tumor Cell Proliferation and Poor Prognosis in Prostate Cancer," *Clin. Cancer Res.*, 16(5): 1553-60, American Association for Cancer Research, United States (2010).

National Comprehensive Cancer Network (NCCN), NCCN Guidelines®, Version 2.2015, Uterine Neoplasms, Accessed at http://www.nccn.org/professionals/physician_gls/PDF/uterine.pdf on Sep. 15, 2015.

Nolting, B., "Linker Technologies for Antibody-Drug Conjugates," *Methods In Molecular Biology-Antibody-Drug Conjugates* 1045:71-100, Humana Press, United States (2013).

Popowycz, F. et al., "Synthesis and reactivity of 4-, 5- and 6-azaindoles," *Tetrahedron* 63(36): 8689-8707, Elsevier Ltd., The Netherlands (2007).

Ramanathan, R.K., et al., "Low Overexpression of HER-2/PPPNeu in Advanced Colorectal Cancer Limits the Usefulness of Trastuzumab (Herceptin®) and Irinotecan as Therapy. A Phase II Trial," *Cancer Invest.* 22(6): 858-865, Marcel Dekker, United States (2004).

Ray-Coquard, I., et al., "HER2 Overexpression/Amplification and Trastuzumab Treatment in Advanced Ovarian Cancer: A GINECO Phase II Study," *Clin. Ovarian Cancer*, 1(]): 54-59, Elsevier, The Netherlands (2008).

Santin, A.D., et al., "Overexpression of HER-2/Neu in Uterine Serous Papillary Cancer," *Clin. Cancer Res.*, 8: 1271-1279, American Association for Cancer Research, United States (2002).

Santin, A.D., et al., "Trastuzumab Treatment in Patients With Advanced or Recurrent Endometrial Carcinoma Overexpressing HER2/neu," *Int. J. Gynecol. Obstet.* 102: 128-131, Elsevier Ireland Ltd., The Netherlands (2008).

Scholl, S., et al., "Targeting HER2 in Other Tumor Types," *Ann. Oncol.*, 12(Suppl. 1): S81-S87, Kluwer Academic Publishers, The Netherlands (2001).

Seo, A.N., et al., "HER2 Status in Colorectal Cancer: Its Clinical Significance and the Relationship between HER2 Gene Amplification and Expression," *PloS One*, 9(5): e98528, Public Library of Science, United States (May 2014).

Shariat, S.F., et al., "Preoperative Plasma HER2 and Epidermal Growth Factor Receptor for Staging and Prognostication in Patients with Clinically Localized Prostate Cancer," *Clin. Cancer Res.*, 13(18): 5377-84, American Association for Cancer Research, United States (2007).

Shen, B-Q., et al., "Conjugation Site Modulates the In Vivo Stability and Therapeutic Activity of Antibody-Drug Conjugates," *Nature Biotechnology* 30(2): I 84-189, Nature Publishing Group, United States (2012).

Shigematsu, H., et al., "A Case OfHER-2-Positive Recurrent Breast Cancer Showing a Clinically Complete Response to Trastuzumab-Containing Chemotherapy After Primary Treatment of Triple-Negative Breast Cancer," *World Journal of Surgical Oncology* 9:146, Biomed Central Ltd., England (2011).

Slomovitz, B.M., et al., "Her-2/neu Overexpression and Amplification in Uterine Papillary Serous Carcinoma," *J. Clin. Oncol.* 22(15): 3126-3132, American Society of Clinical Oncology, United States (2004).

Suzuki, M., et al., "HER2 gene mutations in non-small cell lung carcinomas: Concurrence with her2 gene amplification and her2 protein expression and phosphorylation," *Lung Cancer.* 87(1):14-22, Elsevier Ireland Ltd., The Netherlands (Jan. 2015).

Synthon, "Synthon Biopharmaceuticals reports positive early results with its second generation HER2-antibody-drug conjugate", Jan. 22, 2013, Accessed at http://www.synthon.com/Corporate/News/PressReleases/Synthon-reports-positive- early-results-with-its-second-generation-HER2-antibody-drug-conjugate.aspx on Sep. 1, 2015.

Takezawa, K., et al., "HER2 amplification: a potential mechanism of acquired resistance to EGFR inhibition in EGFR-mutant lung cancers that lack the second-site EGFRT790M mutation," *Cancer Discov.* 2(10): 922-33, American Association for Cancer Research, United States (2012).

Tietze et. al. "Determination of the Biological Activity and Structure Activity Relationships of Drugs Based on the Highly Cytotoxic Duocarmycins and CC-1065," *Toxins* 1: 134-150, MDPI AG, Switzerland (2009).

Trail, P.A., "Antibody Drug Conjugates as Cancer Therapeutics", *Antibodies* 2(1):113-129, MDPI AG, Switzerland (Feb. 2013).

Tsai, C.-M., et al., "Correlation of Intrinsic Chemoresistance of Non-Small-Cell Lung Cancer Cell Lines With HER-2/neu Gene Expression but Not With ras Gene Mutations," *J Natl. Cancer Inst.*, 85(11): 897-901, Oxford University Press, England (1993).

Vippagunta et al. "Crystalline Solids," *Advanced Drug Delivery Reviews* 48(1): 3-26, Elsevier Science B.V., The Netherlands (2001).

Website: Champions Oncology, "Predictive value" Accessed at http://web.archive.org/web/20111204221017/http:/www.championsoncology.com/translationaloncologysolutions/oredictivevalue on Sep. 15, 2015.

Amishiro, N. et al., "New Water-Soluble Duocarmycin Derivatives: Synthesis and Antitumor Activity of A-Ring Pyrrole Compounds Bearing P-Heteroarylacryloyl Groups," *Journal of Medicinal Chemistry* 42(4):669-676,American Chemical Society, United States (1999).

Amishiro, N. et al., "Synthesis and Antitumor Activity of Duocarmycin Derivatives: A-Ring Pyrrole Compounds Bearing P-(5',6',7'-Trimethoxy-2'-indolyl)acryloyl Group," *Bioorganic & Medicinal Chemistry* 8(7):1637-1643, Elsevier Science Ltd., England (2000).

Atwell, G.J. et al., "5-Amino-l-(chloromethyl)-1,2-dihydro-3H-benz[e]indoles: Relationships between Structure and Cytotoxicity for Analogues Bearing Different DNA Minor Groove Binding Subunits," *Journal of Medicinal Chemistry* 42(17):3400-3411, American Chemical Society, United States (1999).

Boger, D.L. et al., "Synthesis and Evaluation of a Series of C3-Substituted CBI Analogues of CC-1065 and the Duocarmycins," *The Journal of Organic Chemistry* 66(15):5163-5173, American Chemical Society, United States (2001).

Jeffrey, S.C. et al., "Design, Synthesis, and in Vitro Evaluation of Dipeptide-Based Antibody Minor Groove Binder Conjugates," *Journal of Medicinal Chemistry* 48(5):1344-1358, American Chemical Society, United States (2005).

Parrish, J.P. et al., "Establishment of Substituent Effects in the DNA Binding Subunit of CBI Analogues of the Duocarmycins and CC-1065," *Bioorganic & Medicinal Chemistry* 11(17):3815-3838, Elsevier Ltd., England (2003).

Parrish, J.P. et al., "Synthesis and Evaluation of N-aryl and N-alkenyl CBI Derivatives," *Bioorganic& Medicinal Chemistry* 12(22):5845-5856,Elsevier Ltd., England (2004).

Schuster, H.J. et al., "Synthesis of the First Spacer Containing Prodrug of a Duocarmycin Analogue and Determination of Its Biological Activity," *Organic & Biomolecular Chemistry* 8(8):1833-1842, Royal Society of Chemistry, England (2010).

Tietze, L.F. et al., "A Strategy for Tumor-Selective Chemotherapy by Enzymatic Liberation of seco-duocarmycin SA-Derivatives from Nontoxic Prodrugs," *Bioorganic & Medicinal Chemistry* 9:1929-1939, Elsevier Science Ltd., England (2001).

(56) References Cited

OTHER PUBLICATIONS

Tietze, L.F. et al., "Highly Selective Glycosylated Prodrugs of Cytostatic CC-1065 Analogues for Antibody-Directed Enzyme Tumor Therapy," *ChemBioChem* 2(10):758-765, Wiley-VCH-Verlag GmbH, Germany (2001).

Tietze, L.F. et al., "Synthesis and Biological Evaluation of Novel Analogues and Prodrugs of the Cytotoxic Antibiotic CC-1065 for Selective Cancer Therapy," *European Journal of Organic Chemistry* 10:1634-1645, Wiley-VCH Verlag GmbH, Germany (2002).

Tietze, L.F. et al., "Antitumor Agents: Development of Highly Potent Glycosidic Duocarmycin Analogues for Selective Cancer Therapy," *Angewandte Chemie International Edition* 45:6574-6577, Wiley-VCH Verlag GmbH & Co. KGaA, Germany (2006).

Tietze, L.F. et al., "Selective Treatment of Cancer: Synthesis, Biological Evaluation and Structural Elucidation of Novel Analogues of the Antibiotic CC-1065 and the Duocarmycins," *Chemistry—A European Journal* 13(16):4396-4409, Wiley-VCH Verlag GmbH, Germany (2007).

Tietze, L.F. et al., "Asymmetric Synthesis and Biological Evaluation of Glycosidic Prodrugs for a Selective Cancer Therapy," *ChemMedChem* 3(12):1946-1955, Wiley-VCH Verlag GmbH & Co. KGaA, Germany (2008).

Wang, Y. et al., "Design, Synthesis, Cytotoxic Properties and Preliminary DNA Sequencing Evaluation of CPI-N-methylpyrrole Hybrids. Enhancing Effect of a trans Double Bond Linker and Role of the Terminal Amide Functionality on Cytotoxic Potency," *Anti-Cancer Drug Design* 11(1):15-34, Oxford University Press, United States (1996).

Wang, Y. et al., "CC-1065 Analogues Bearing Different DNA-Binding Subunits: Synthesis, Antitumor Activity, and Preliminary Toxicity Study," *Journal of Medicinal Chemistry* 46(4):634-637, American Chemical Society, United States (2003).

Cumnock, K., et al., "Trisulfide Modification Impacts the Reduction Step in Antibody-Drug Conjugation Process," *Bioconjugate Chemistry* 24(7):1154-1160, American Chemical Society, United States (2013).

Dokter, W.H.A., et al., "Abstract 2652: In vitro and in vivo antitumor activity of SYD985, a novel HER2-targeting ADC: a comparison with T-DM1," *Cancer Research* 74(Suppl 19):Abstract 2652, Proceedings of the 105$^{th}$ Annual Meeting of the American Association for Cancer Research, Apr. 5-9, 2014, San Diego, CA (Oct. 1, 2014).

Foulkes, W.D., et al., "Triple-Negative Breast Cancer," *The New England Journal of Medicine* 363:1938-1948, Massachusetts Medical Society, United States (2010).

Hamblett, K.J., et al., "Effects of Drug Loading on the Antitumor Activity of a Monoclonal Antibody Drug Conjugate," *Clinical Cancer Research* 10(20):7063-7070, American Association for Cancer, United States (2004).

Kovtun, Y.V. and Goldmacher, V.S., "Cell killing by antibody-drug conjugates," *Cancer Letters* 255(2):232-240, Elsevier Ireland Ltd., Ireland (2007).

Mcdonagh, C.F., et al., "Engineered antibody-drug conjugates with defined sites and stoichiometries of drug attachment," *Protein Engineering, Design & Selection* 19(7):299-307, Oxford University Press, England (2006).

Muller, U., "Polymorphism," in *Inorganic Structural Chemistry*, pp. 14-15, John Wiley & Sons Ltd, England (1993).

Ouyang, J., "Drug-to-antibody ratio (DAR) and drug load distribution by hydrophobic interaction chromatography and reversed phase high-performance liquid chromatography," *Methods in Molecular Biology* 1045:275-283, Springer Science+Business Media, LLC, England (2013).

Sun, M.M.C., et al., "Reduction-Alkylation Strategies for the Modification of Specific Monoclonal Antibody Disulfides," *Bioconjugate Chem.* 16(5):1282-1290, American Chemical Society, United States (2005).

Greenwald, R.B., et al., "Effective drug delivery by PEGylated drug conjugates," *Advanced Drug Delivery Reviews* 55(2):217-250, Elsevier Science B.V., Netherlands (2003).

Van Der Lee, M., et al., "Poster 2652:The HER2-targeting ADC SYD985 shows superior antitumor activity compared to T-DM1 in preclinical studies with an activity profile that includes low-HER2 expressing breast cancers," AACR Annual Meeting 2014, Apr. 5-9, 2014, San Diego, CA.

Van Der Lee, M.M., et al., "The Preclinical Profile of the Duocarmycin-Based HER2-Targeting ADC SYD985 Predicts for Clinical Benefit in Low HER2-Expressing Breast Cancers," *Mol Cancer Ther.* 14(3):692-703, American Association for Cancer Research, United States (published online Jan. 14, 2015).

Verheijden, G., et al., "Poster 850294: Preclinical Data of SYD985 Support the Clinical Investigation of This Novel Anti-HER2 Antibody-Drug Conjugate in Breast Cancer Patients with Low Levels of HER2 Expression," 2014 San Antonio Breast Cancer Symposium, (Dec. 2014).

International Search Report and Written Opinion for International Application No. PCT/EP2015/050304, European Patent Office, Rijswijk, Netherlands, dated Jul. 10, 2015, 12 pages.

El-Sahwi, K.S., et al., "Development of targeted therapy in uterine serous carcinoma, a biologically aggressive variant of endometrial cancer," *Expert Rev Anticancer Ther.* 12(1):41-49, Expert Reviews Ltd., England (2012).

Junutula, J.R., et al., "Site-specific conjugation of a cytotoxic drug to an antibody improves the therapeutic index," *Nature Biotechnology* 26(8):925-932, Nature Publishing Group, England (2008).

Tietze, L.F., et al., "Synthesis of Fluorescence-Labelled Glycosidic Prodrugs Based on the Cytotoxic Antibiotic Duocarmycin," *Eur. J. Org. Chem.* 2010(36):6909-6921, Wiley-VCH Verlag GmbH & Co., Germany (2010).

Tietze,L.F.,etal.,"Enantio-andDiastereoselectiveSynthesisof Duocarmycine-Based Prodrugs for a Selective Treatment of Cancer by Epoxide Opening," *Chemistry—A European Journal* 14(3):895-901, Wiley-VCH Verlag GmbH & Co., Germany (2008).

Tietze, L.F., et al., "Atropisomerism of Aromatic Carbamates," *Chemistry—A European Journal* 16(42):12678-12682, Wiley-VCH Verlag GmbH & Co., Germany (2010).

Sigma-Aldrich Co. LLC, "Product Information," Catalog No. B3773, sigma-aldrich.com, accessed at https://www.sigmaaldrich.com/content/dam/sigma-aldrich/docs/Sigma/Datasheet/b3773dat.ndf, accessed on Apr. 20, 2017, 1 page.

Moussaid, Y. et al., "Trastuzumab therapy in metastatic bladder carcinoma: The proof of concept," *Journal of Cancer Research Therapy* 2(8):128-131, Moussaid Y. et al., France (2014).

Peyromaure M., et al., "Trastuzumab (Herceptin™) in Metastatic Transitional Cell Carcinoma of the Urinary Tract: Report on Six Patients," *European Urology* 48:771-778, Elsevier B.V., Netherlands (2005).

Oudard, S. et al., "Multicenter Randomized Phase 2 Trial of Gemcitabine-Platinum with or without Trastuzumab (T) in Advanced/Metastatic Urothelial Carcinoma (A/MUC) with HER2 Overexpression," *Annals of Oncology* 23 Suppl. 9, Abstract No. 7860, ESMO 2012 Congress, Vienna, Austria (2012).

Wendling, "Trastuzumab Role May Be Limited in HER2-Positive Bladder Cancer," *MDedge—Hemotology & Oncology*, Oct. 25, 2012.

Koshkin et al., "Systemic Review: Targeting HER2 in Bladder Cancer," *Bladder Cancer* 5 (2019) 1-12.

Banerji et al., "Trastuzumab duocarmazine in locally advanced and metastatic solid tumours and HER2-expressing . . . ," *Lancet Oncol*, Jun. 27, 2019 (with Supplemental Appendix).

\* cited by examiner

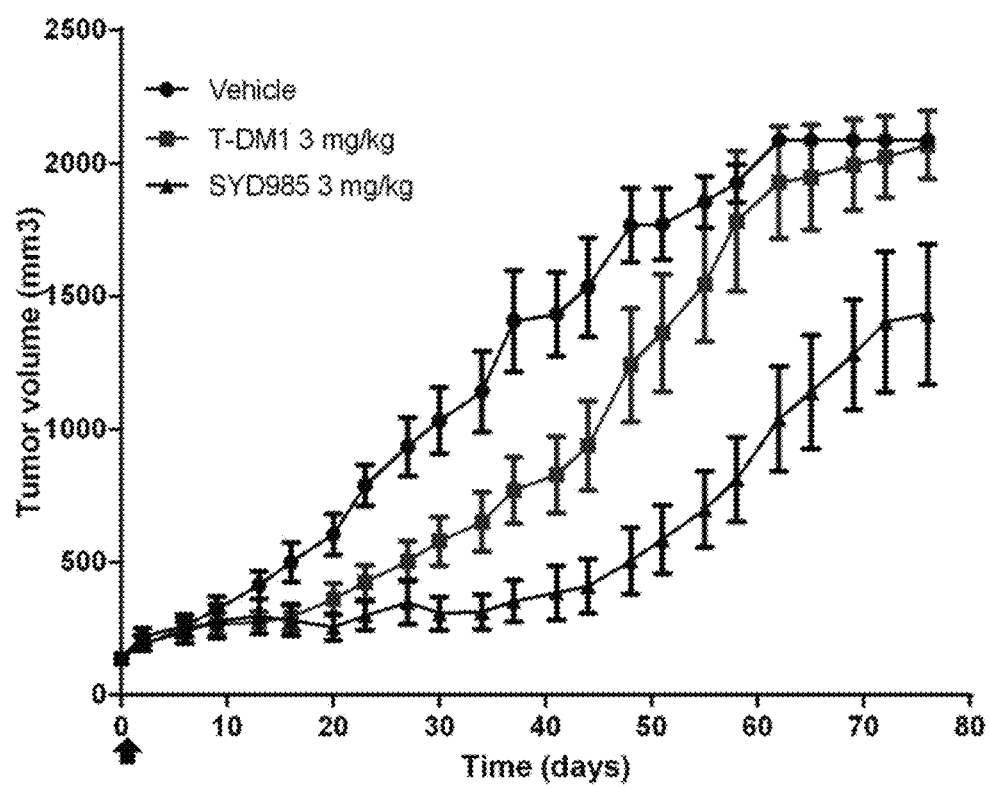
Figure 1. MAXF 1162 PDX

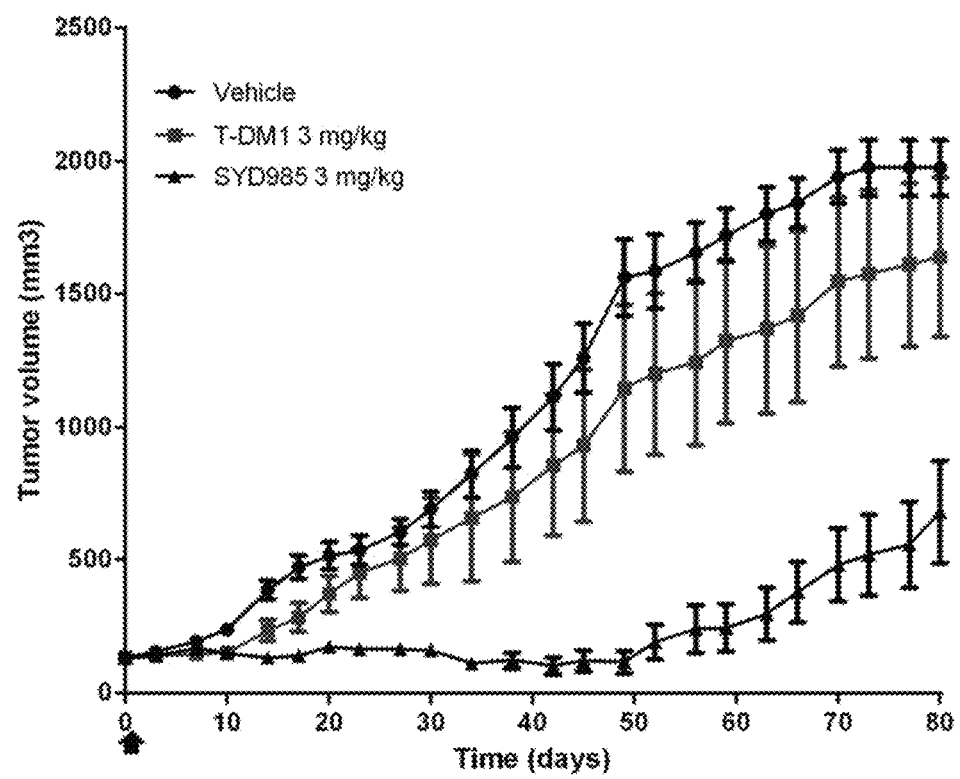
Figure 2. HBCx-34 PDX

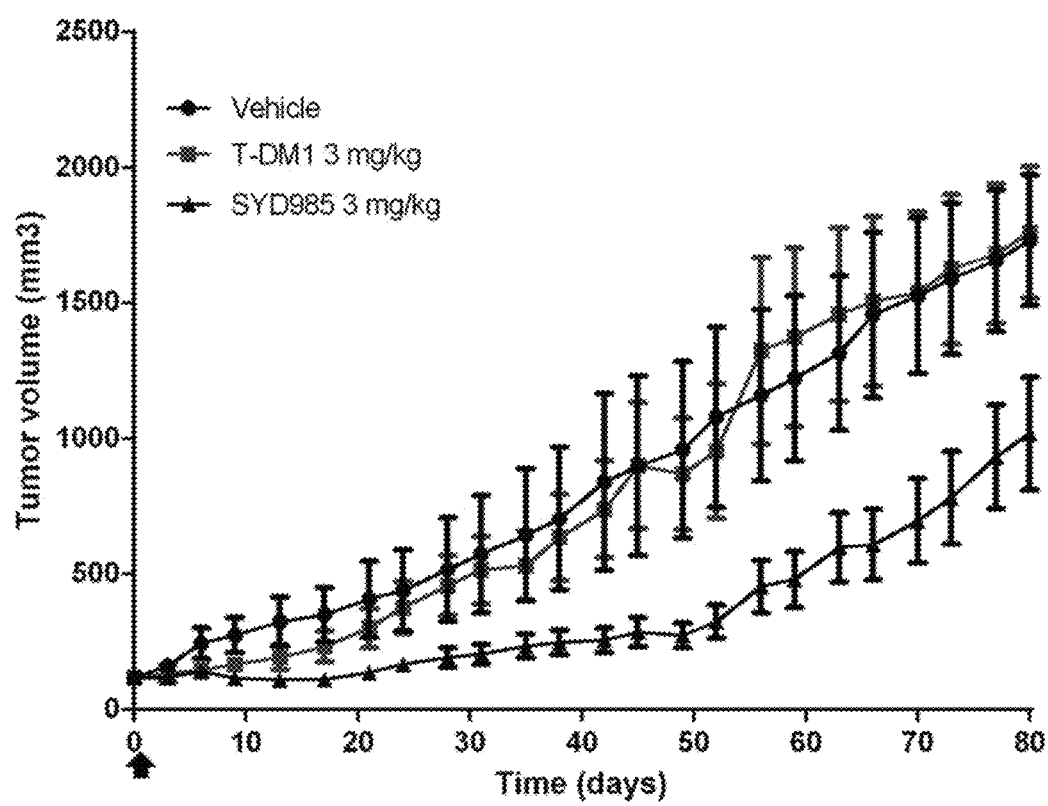
Figure 3. MAXF 449 PDX

Figure 4. HBCx-10 PDX
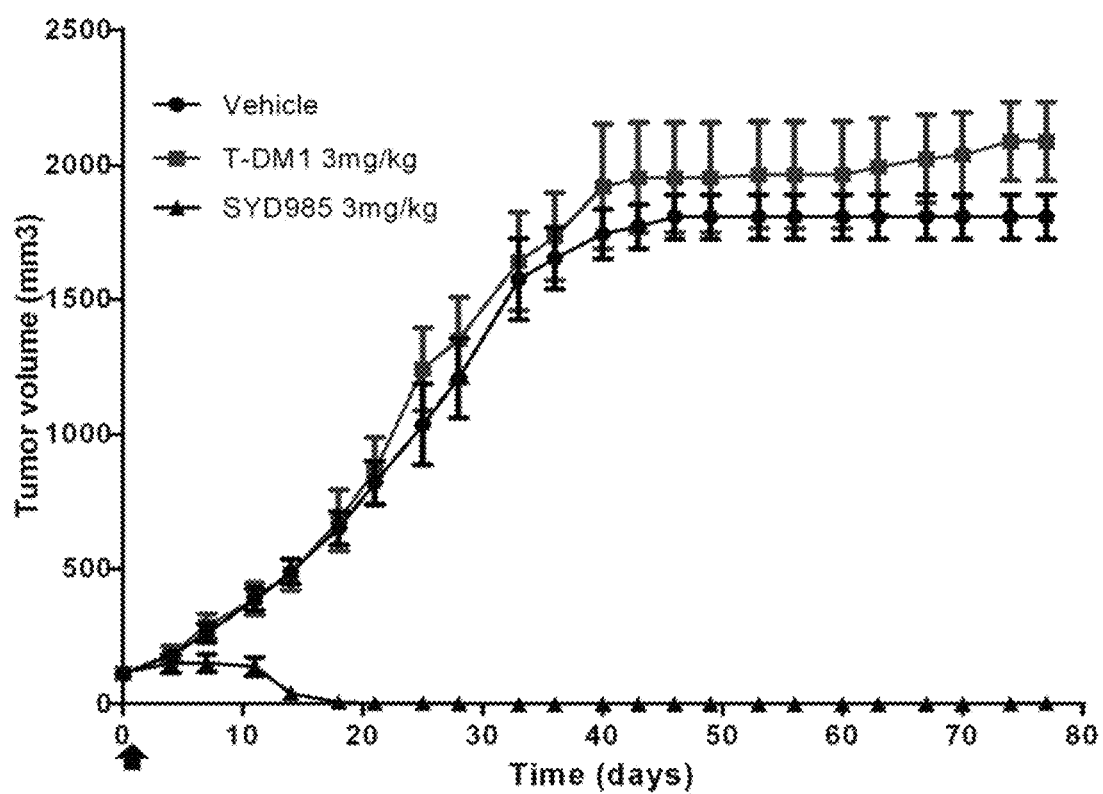

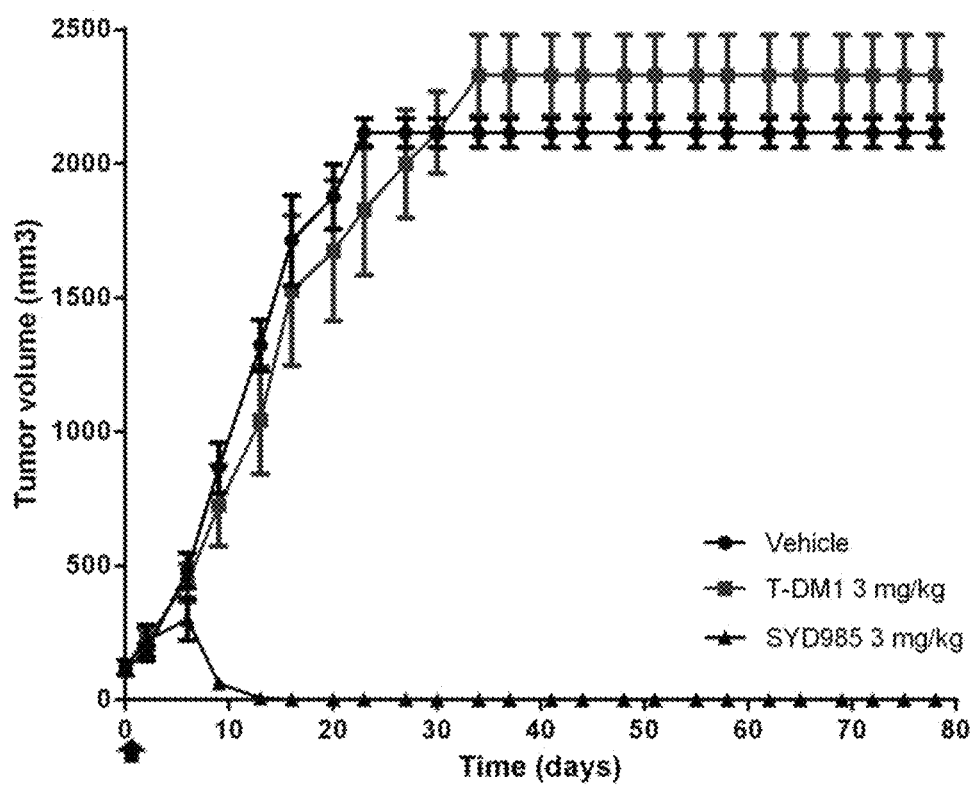
Figure 5. MAXF-MX1 PDX

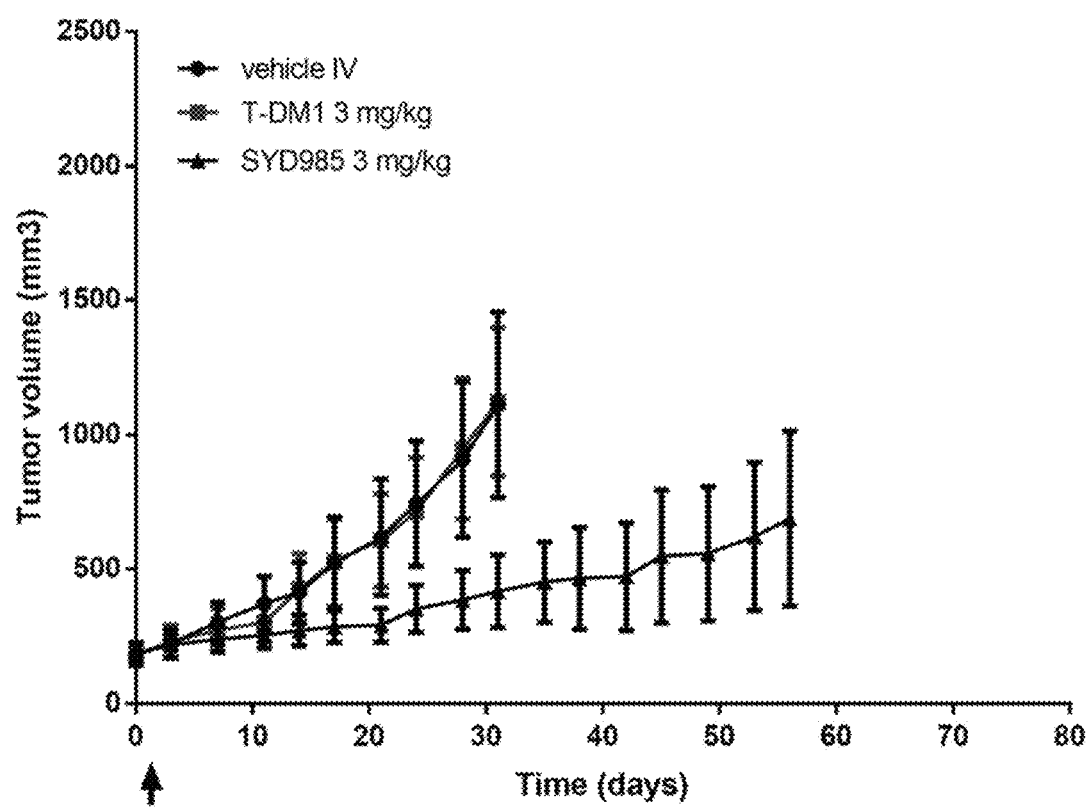
Figure 6. ST313 PDX

Figure 7. GXA3057 PDX
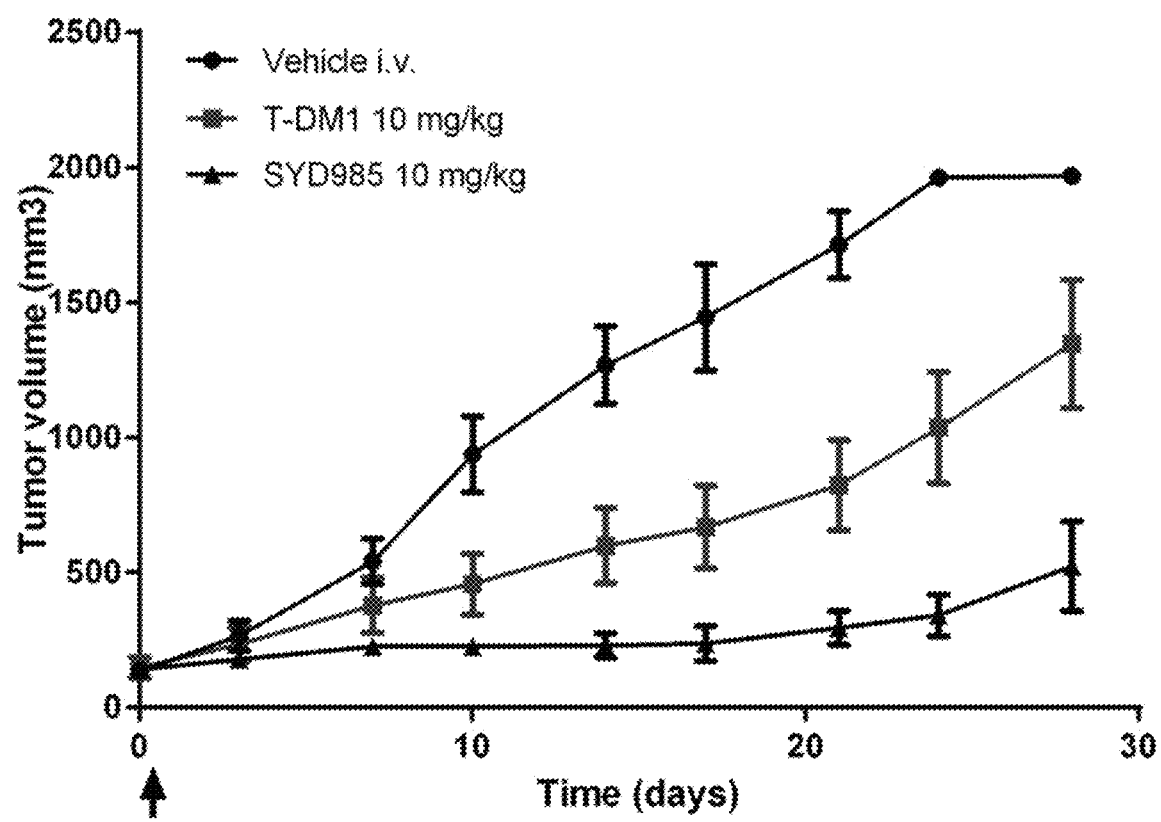

Figure 8. GXA3067 PDX
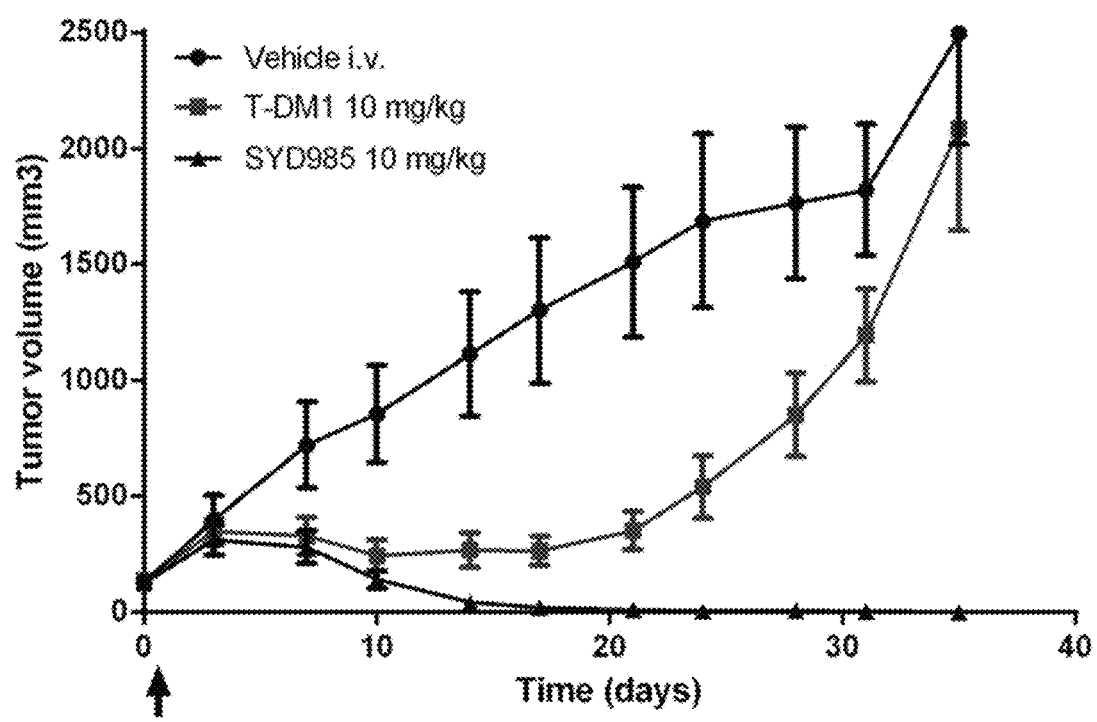

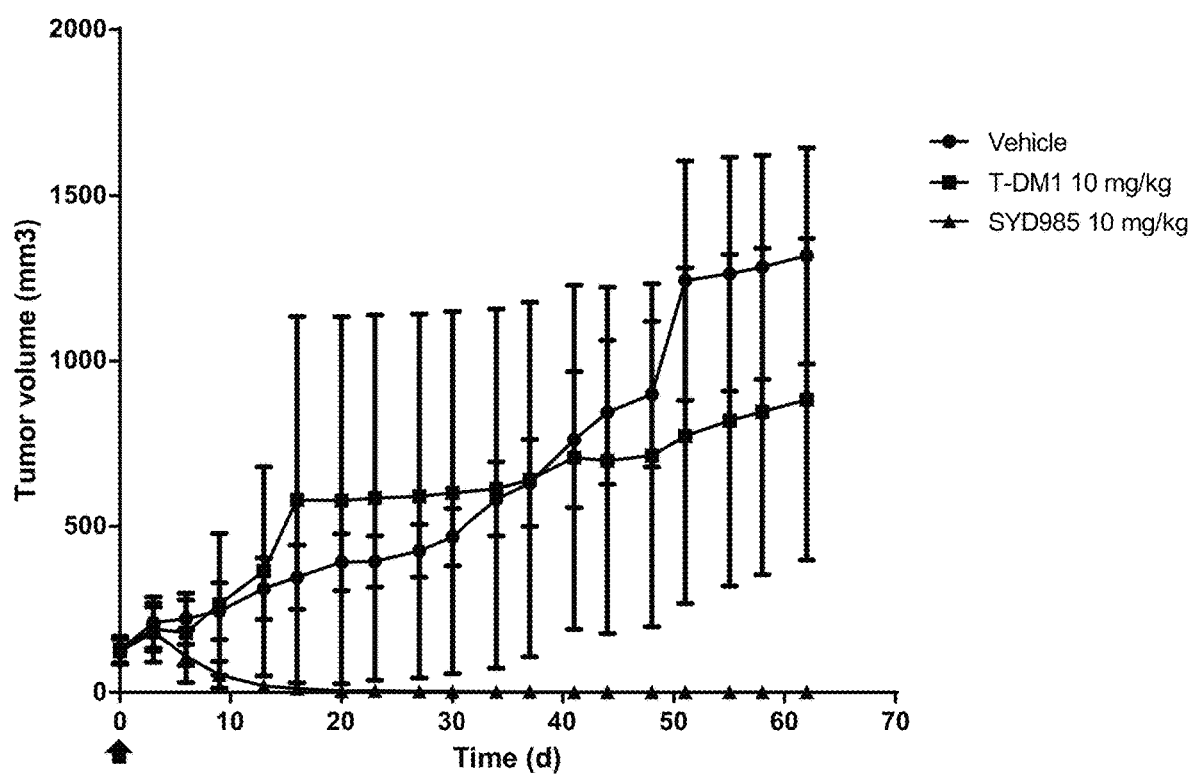
Figure 9. GXA3054 PDX

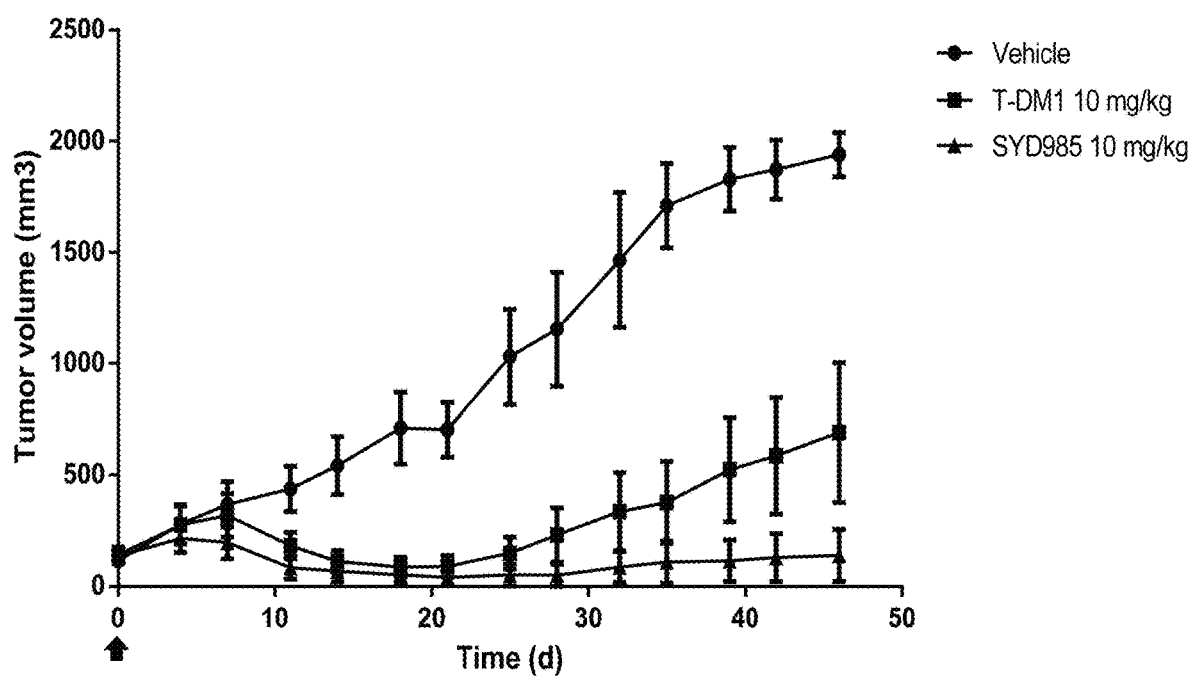
Figure 10. GXA3038 PDX

Figure 11. BXF439 PDX
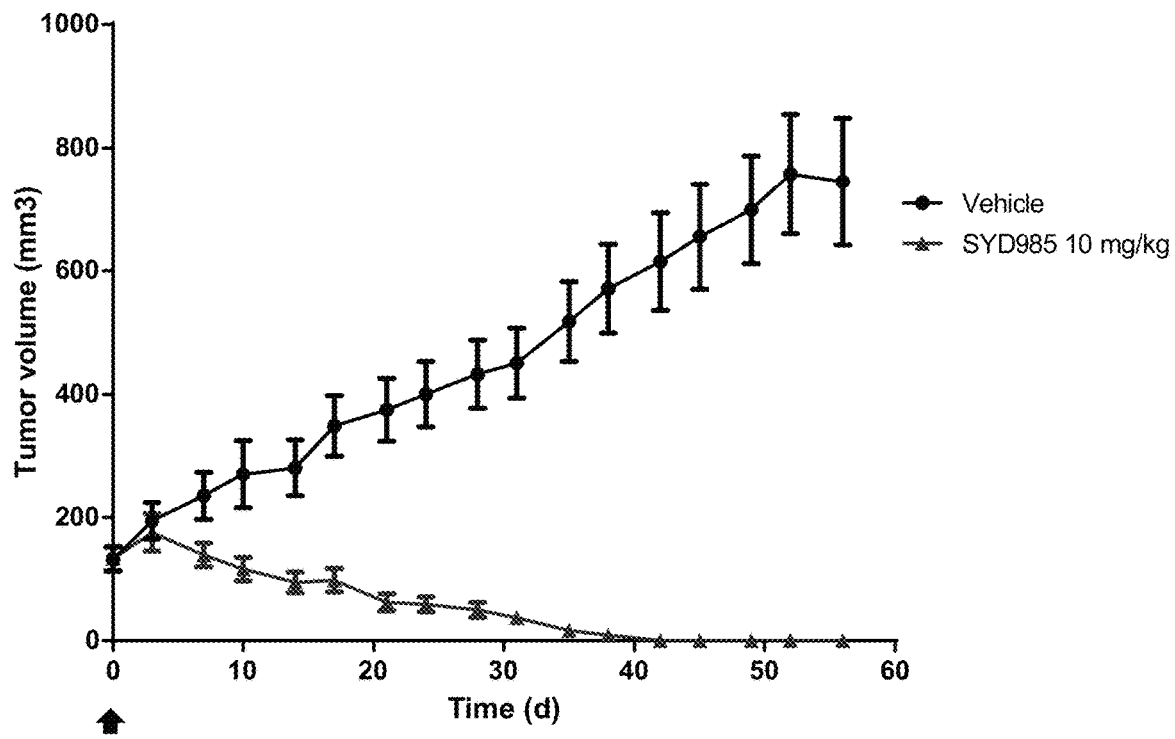

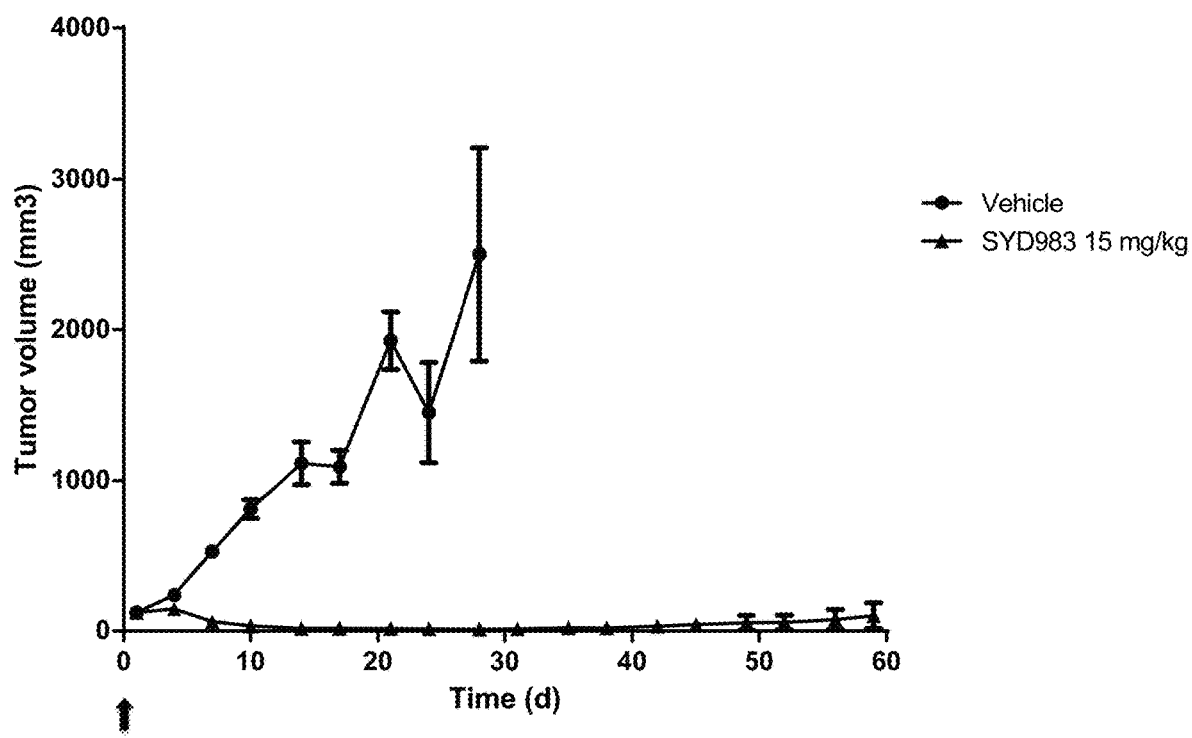
Figure 12. SKOV3 cell line-derived xenograft

DUOCARMYCIN ADCS SHOWING IMPROVED IN VIVO ANTITUMOR ACTIVITY

CROSS REFERENCE TO RELATED APPLICATIONS

The present application is a continuation under 35 U.S.C. § 120 of copending U.S. application Ser. No. 15/798,695, filed Oct. 31, 2017, which is a divisional under 35 U.S.C. § 120 of U.S. application Ser. No. 15/216,407, filed Jul. 21, 2016 (now abandoned), which is a divisional of U.S. application Ser. No. 14/859,201, filed Sep. 18, 2015 (now U.S. Pat. No. 9,421,278), which is a continuation of PCT International Application No. PCT/EP2015/050350, filed Jan. 9, 2015, which claims the benefit of priority to European Application No. 14150791.3, filed on Jan. 10, 2014, and to EP 14188450.2, filed on Oct. 10, 2014; the disclosure of each prior U.S. application is incorporated by reference herein in its entirety.

FIELD OF THE INVENTION

The present invention relates to duocarmycin-containing antibody-drug conjugates (ADCs) for use in the treatment of human solid tumours and haematological malignancies expressing human epidermal growth factor receptor 2 (HER2), in particular breast cancer, gastric cancer, bladder cancer, ovarian cancer, lung cancer, prostate cancer, pancreatic cancer, colorectal cancer, head and neck squamous cell cancer, osteosarcoma, and acute lymphoblastic leukaemia.

BACKGROUND OF THE PRESENT INVENTION

Antibodies have been conjugated to a variety of cytotoxic drugs, including small molecules that alkylate or crosslink DNA (e.g. duocarmycins and calicheamicins or pyrrolobenzodiazepine dimers, respectively), or disrupt microtubules (e.g. maytansinoids and auri-statins) or bind DNA (e.g. anthracyclines). One such ADC comprising a humanized anti-CD33 antibody conjugated to calicheamicin—Mylotarg™ (gemtuzumab ozogamicin, Wyeth)—was approved in 2000 for acute myeloid leukaemia. In 2011, the US Food and Drug Administration (FDA) approved Adcetris™ (brentuximab vedotin, Seattle Genetics), an ADC comprising a chimeric antibody to CD30 conjugated to monomethyl auristatin E (MMAE) for treatment of Hodgkin's lymphoma and anaplastic large cell lymphoma.

Duocarmycins, first isolated from a culture broth of *Streptomyces* species, are members of a family of antitumor antibiotics that include duocarmycin A, duocarmycin SA, and CC-1065. These extremely potent agents allegedly derive their biological activity from an ability to sequence-selectively alkylate DNA at the N3 position of adenine in the minor groove, which initiates a cascade of events leading to tumour cell death.

WO2011/133039A discloses a series of novel analogues of the DNA-alkylating agent CC-1065 and HER2-targeting ADCs thereof. In Example 15, a number of trastuzumab-duocarmycin conjugates were tested against N87 (i.e. HER2 IHC (immunohistochemistry) 3+ gastric tumour) xenografts in nude mice. The results are shown in FIGS. 4A, 4B and 4C. After treatment with a single dose of 12 mg/kg i.v., all six ADCs reduced the tumour volume and improved survival compared to the antibody trastuzumab itself and control vehicle, without negatively affecting body weight. It was concluded that conjugates that contain a relatively short linker have a better (antitumor) efficacy than the corresponding conjugate with a relatively long linker, and that both the nature of the linker and the nature of the drug were demonstrated to have an effect on efficacy as well.

Breast cancer remains the most common malignancy among women worldwide. Breast cancer is a heterogeneous disease, which exhibits a wide range of clinical behaviours and prognoses. Breast cancer is an abnormal malignant growth of epithelial cells of the milk lobules or ducts of the mammary gland. The cancer tissue can be exclusively located on the place of origin (cancer in situ) or can have invaded through the basement membrane into the surrounding tissue (invasive cancer). Metastatic cancer occurs as soon as the cancer cells have spread by way of lymph and blood vessels to other organs. Histological differentiation and characterization of the breast cancer cells is performed with use of biomarkers.

Molecular classification of breast cancer for therapeutic decisions mainly consists of the assessment of the estrogen receptor (ER), progesterone receptor (PR), and human epidermal growth factor receptor 2 (HER2) expression status. This implies that globally three types of breast cancer can be discerned: (1) breast cancer tissue with expression of hormone receptor (ER or PR) without over-expression of HER2, (2) breast cancer tissue with over-expression of HER2, with or without expression of hormone receptor (HR), and (3) breast cancer tissue that has no therapeutically relevant hormone receptor or HER2 receptor expression, so-called triple negative breast cancer (TNBC).

Breast cancer patients with hormone receptor (HR) positive cancer tissue status (ca. 60-70% of all breast cancer patients) have a better prognosis than those without or with minimal hormone receptor status. On the contrary, patients whose tumour has an IHC 3+ or IHC 2+/FISH (fluorescence in situ hybridization) positive status (occurring in about 20% of all breast cancer cases) have a worse prognosis in comparison with breast cancer patients whose tumour has a lower grade of HER2 membrane expression or a FISH negative amplification rate. Now that patients with hormone receptor positive and HER2 over-expressing breast cancer tissue have the option of targeting therapy, triple negative breast cancer implies the worst prognosis, as only chemotherapy with limited efficacy is available for these patients whose tumour is ER, PR and HER2 negative.

Herceptin™ (trastuzumab), a recombinant humanized IgG1 monoclonal antibody against HER2, was approved in the US by the FDA in 1998 for adjuvant treatment of HER2 over-expressing breast cancer and for the treatment of metastatic HER2 over-expressing breast cancer and gastric cancer, i.e. HER2 IHC 3+ or HER2 IHC 2+/FISH positive. The drug was approved in Europe by the EMA in 2000.

Clinical studies with patients who have metastatic breast cancer disease have demonstrated, that there is only clinical relevant efficacy of trastuzumab treatment if the patient has a tumour with HER2 IHC over-expression or FISH positive gene amplification. For this reason, current HER2 testing algorithms are aimed at identifying those patients most likely to achieve a significant benefit from HER2 targeting. Whereas HER2 membrane expression is biologically a continuum from low to high over-expression, approved IHC tests, like the HercepTest™ (Dako, Glostrup, Denmark), categorize HER2 status on a semi-quantitative scale ranging from 0 to 3+. An IHC score of 3+ is assigned if there is a strong circumferential membrane staining in >10% of the cancer cells. FISH positive gene amplification is assigned if the amplification rate relative to the centromere is >2.0. It identifies patients who might have a benefit of treatment with trastuzumab or other HER2 targeting agents. A review of 6,556 breast cancers revealed that about 92% of tumours with a HER2 score of 3+ had FISH positive gene amplification. Conversely, HER2 amplification was observed at lower rates in tumours with scores of 2+(23.3%), 1+(7.4%), and 0 (4.1%). With HER2 amplification as an established predictor of response to HER2 targeting agents, the current algorithm calls for FISH testing of tumours with a HER2 IHC score of 2+.

Ado-trastuzumab emtansine or trastuzumab emtansine (Kadcyla™, T-DM1) is an ADC in which trastuzumab is conjugated to the cytotoxic maytansine anti-tubulin agent DM1. T-DM1 has antitumor activity in tumour xenograft models that are not responding to therapy with trastuzumab as single agent. In the Phase 3 EMILIA trial, patients with HER2 positive advanced breast cancer, previously treated with trastuzumab and a taxane, were randomly assigned to receive T-DM1 or lapatinib plus capecitabine. T-DM1 treatment effectuated significantly longer progression-free and overall survival time in comparison to the treatment of the control group.

Kadcyla™ (T-DM1) was approved in the US by the FDA in February 2013 for the treatment of patients with HER2-positive metastatic breast cancer who received prior treatment with trastuzumab and a taxane. The drug was approved in Japan by the MHLW (Ministry of Health, Labour and Welfare) in September 2013 and in Europe by the EMA in November 2013. The currently approved regimen comprises a dosage of 3.6 mg/kg body weight i.v. every three weeks. A dosage of 2.4 mg/kg body weight i.v. weekly is investigated in an ongoing Phase II study with a combination of T-DM1 and capecitabine for the $2^{nd}$ line treatment of patients with breast cancer or gastric cancer and in an ongoing Phase III study to investigate T-DM1 against a taxane as $2^{nd}$ line treatment of patients with gastric cancer. A Phase III study is also ongoing for the combination of T-DM1 with pertuzumab for the treatment of patients with HER2 positive, locally advanced, or metastatic breast cancer.

Despite the improvement that the introduction of T-DM1 in clinical practice brought over trastuzumab for the treatment of HER2-positive metastatic breast cancer, the use of T-DM1 is associated with a number of serious side-effects, most importantly thrombocytopenia, hepatotoxicity, and neuropathy (irreversible axonal degeneration). Furthermore, neither trastuzumab nor T-DM1 are authorized for the treatment of human solid tumours and haematological malignancies with moderate or low HER2 expression, i.e. IHC 2+ or 1+ and/or FISH negative HER2 amplification status of the cancer tissue.

In analogy to breast cancer, HER2 expression indicates a poor prognosis for patients with ovarian cancer (A. Berchuck et al., 1990, Cancer Res., 50, 4087-4091; H. Meden and W. Kuhn, 1997, Eur. J. Obstet. & Gynecol. Reprod. Biol., 71, 173-179). SKOV3 cells are derived from the ascites fluid of a patient with ovarian adenocarcinoma. This cell line is over-expressing HER2 and is frequently used for in vitro and in vivo explorative investigation of HER2 targeting agents. Trastuzumab and pertuzumab have several anti-cancer effects in this cell line (N. Gaborit et al., 2011, J. Biol. Chem., 286, 13, 11337-11345). Monotherapy with the anti-HER2 antibodies trastuzumab and pertuzumab thus far had modest efficacy (G. M. Mantia-Smaldone et al., 2011, Cancer Management Res. 3, 25-38; S. P. Langdon et al., 2010, Expert Opin. Biol. Ther. 10:7, 1113-1120). The antitumor effect is markedly increased if a HER2 targeting antibody is combined with chemotherapy (S. Makhija et al., 2010, J. Clin. Oncol., 28:7, 1215-1223; I. Ray-Coquard et al., 2008, Clin. Ovarian Cancer, 1:1, 54-59).

Further, a high medical need exists for the treatment of late stage bladder cancer disease. Chemotherapy, e.g. the combination of cisplatin and gemcitabine for advanced or metastatic bladder cancer, has limited efficacy as it effectuates in the mean a response rate under 50%, whereas patients have an overall survival time of 6 to 12 months. In case of resistance to chemotherapy there is no standard therapy option at all. HER2 positivity was significantly associated with reduced complete response rates (50% versus 81%, p=0.026) after chemo-radiation (A. Chakravarti et al., 2005, Int. J. Radiation Oncology Biol. Phys., 62:2, 309-317). Addition of trastuzumab to a regimen of paclitaxel and carboplatin as first line therapy of HER2 positive advanced bladder cancer showed an overall response rate of 70% and an overall survival time of 14.1 months in a Phase II study (M. H. A. Hussain et al., 2007, J. Clin. Oncol., 25:16, 2218-24). In a casuistic application, a patient with a tumor relapse after standard chemotherapy responded to the combination of trastuzumab, paclitaxel and carboplatin (D. Amsellem-Ouazana et al., 2004, Ann. Oncol., 15, 3, 538).

In case of invasive non-small-cell lung cancer adenocarcinoma, HER2 mutation and amplification are related with unfavorable outcome (M. Suzuki et al., 2014, Lung Cancer, http://dx.doi.org/10.1016/j.lungca.2014.10.014). In lung cancer patients with HER2 mutation, a disease control rate of 93% could be effectuated with trastuzumab-based therapies (J. Mazieres et al., 2013, J. Clin. Oncol., 31:16, 1997-2004). Chemo-resistance of lung cancer often is associated with enhanced HER2 expression (C.-M. Tsai et al., 1993, J. Natl. Cancer Inst., 85:11, 897-901; Z. Calikusu et al., 2009, J. Exp. Clin. Cancer Res., 28:97) and resistance to tyrosine kinase inhibitors is correlated with enhanced HER2 amplification (K. Takezawa et al., 2012, Cancer Discov. 2(10), 922-33).

Patients with early or advanced prostate cancer mostly receive an androgen receptor targeting therapy. There is a cross-talk in the signaling functions of the androgen receptor and HER2 (F.-N. Hsu et al., 2011, Am. J. Physiol. Endocrinol. Metab., 300:E902-E908; L. Chen et al., 2011, Clin. Cancer Res., 17(19), 6218-28). HER2 activation suppresses the expression of the androgen receptor (C. Cai et al., 2009, Cancer Res., 69(12), 5202-5209), increased HER2 expression is associated with PSA progression, rapid proliferation and poor prognosis (S. Minner et al., 2010, Clin. Cancer Res., 16(5), 1553-60; S. F. Shariat et al., 2007, Clin. Cancer Res., 13(18), 5377-84). Increased expression of HER2 seems to be involved in progression to androgen independence in about a quarter of prostate cancer cases (J. M. S. Bartlett et al., 2005, J. Pathol., 205, 522-529).

Pancreatic cancer is among the most lethal human solid tumors due to its insidious onset and resistance to therapy. Gemcitabine or the combination of 5-FU, leucovorin, irinotecan, and oxaliplatin can help prolong life in patients with advanced disease (H. Burris and A. M. Storniolo, 1997, Eur. J. Cancer 33(1):518-522; T. Conroy et al., 2011, N. Engl. J. Med. 364(19):1817-25). More recently, it was reported that HER2 expression is also prevalent in pancreatic cancer with an equal proportion of 10% designated as HER2 2+ and 3+.

Based on this fact, HER2-targeted treatment comprising trastuzumab is considered as a viable option in this patient population based on effects observed in pre-clinical models [C. Larbouret et al., 2012, Neoplasia 14(2), 121-130).

Using accepted staining and scoring methods, over-expression of HER2 was observed in approximately 6% of colorectal cancer (CRC) patients (A. N. Seo et al., 2014, PLoS ONE, 9(5): e98528). Based on this, HER2-targeting treatment may be effective in this subset of CRC patients. Two clinical trials have investigated the benefit of trastuzumab-containing combination therapy in advanced or metastatic CRC and clinical responses were observed in these trials providing evidence of treatment efficacy (R. K. Ramanathan et al., 2004, Cancer Invest. 22(6): 858-865; J. Clark et al., 2003, Proc. Am. Soc. Clin. Oncol. 22: abstr 3584). Moreover, one study suggested the inclusion of trastuzumab therapy as part of treatment regimens for (anti-EGFR monoclonal antibody) cetuximab-resistant CRC patients (A. Bertotti et al., 2011, Cancer Discov. 1(6): 508-523).

The management of advanced head and neck squamous cell cancer or carcinoma (HNSCC) consists of multiple-modality therapy with surgery, radiation, and chemotherapy. Beckhardt et al. reported high HER2 over-expression in 16% of cell line samples, and moderate and low HER2 expression in 31% and 35% of samples, respectively (R. N. Beckhardt et al., 1995, Arch. Otolaryngol. Head Neck Surg. 121:1265-1270). This illustrates the potential therapeutic potential of trastuzumab treatment in HNSCC.

In 1999, Gorlick et al. reported over-expression of HER2 in 20 of 47 osteosarcoma samples, and showed that these patients had a poor response to therapy and a decreased rate of survival compared with patients whose tumors did not over-express this antigen (R. Gorlick et al., 1999, J. Clin. Oncol. 17:2781-8). Hence, HER2 emerged as a promising candidate for targeted biologic therapy in this indication. Recent findings from clinical investigation using trastuzumab indicate that anti-HER2 treatment can be safely delivered in combination with anthracycline-based chemotherapy and dexrazoxane (D. Ebb et al., 2012, J. Clin. Oncol. 30(20), 2545-2551).

Further, HER2 over-expression is seen in approximately one-third of acute lymphoblastic leukaemia (ALL) patients, even more frequent in the presence of the Philadelphia translocation. Inhibition of HER2 induces apoptosis of the leukemia cells in vitro (M. E. Irwin et al., 2013, PLoS ONE, 8:8, e70608). In a Phase II study, it was demonstrated that trastuzumab treatment of refractory or relapsing adult B-ALL patients with HER2 over-expression in malignant B-cells resulted in an overall response rate of 13%, which shows the response of this disease to a HER2 targeting agent (P. Chevalier et al, Blood, 2012, DOI 10.1182/blood-2011-11-390781).

Hence, there is a need for new HER2-targeted therapies, notably for treating patients with tumours and malignancies that have (i) a moderate or low IHC status, and/or (ii) a negative FISH status, and/or (iii) a hormone receptor (HR) negative status of the cancer tissue. Particularly, new regulatory approved therapies are needed for the targeted treatment of triple negative breast cancer (TNBC).

BRIEF DESCRIPTION OF THE PRESENT INVENTION

The present invention relates to duocarmycin-containing antibody-drug conjugates (ADCs) for use in the treatment of human solid tumours and haematological malignancies expressing HER2, in particular breast cancer, gastric cancer, bladder cancer, ovarian cancer, lung cancer, prostate cancer, pancreatic cancer, colorectal cancer, head and neck squamous cell cancer, osteosarcoma, and acute lymphoblastic leukaemia.

BRIEF DESCRIPTION OF THE DRAWINGS

FIG. 1. Antitumor activity of SYD985 compared to T-DM1 in MAXF-1162 PDX model (breast cancer, adenocarcinoma, HER2 IHC 3+, HER2 FISH positive) (CRO: Oncotest).

FIG. 2. Antitumor activity of SYD985 compared to T-DM1 in HBCx-34 PDX model (breast cancer, ductal carcinoma, HER2 IHC 2+, HER2 FISH negative, ER and PR positive) (CRO: XenTech).

FIG. 3. Antitumor activity of SYD985 compared to T-DM1 in MAXF 449 PDX model (breast cancer, invasive ductal carcinoma, HER2 IHC 1+, HER2 FISH negative, ER and PR negative, i.e. triple negative breast cancer) (CRO: Oncotest).

FIG. 4. Antitumor activity of SYD985 compared to T-DM1 in HBCx-10 PDX model (breast cancer, ductal adenocarcinoma, HER2 IHC 1+, HER2 FISH negative, ER and PR negative, i.e. triple negative breast cancer) (CRO: XenTech).

FIG. 5. Antitumor activity of SYD985 compared to T-DM1 in MAXF-MX1 PDX model (breast cancer, invasive ductal carcinoma, HER2 IHC 1+, HER2 FISH negative, ER and PR negative, i.e. triple negative breast cancer) (CRO: Oncotest).

FIG. 6. Antitumor activity of SYD985 compared to T-DM1 in ST313 PDX model (breast cancer, HER2 IHC 2+, HER2 FISH negative, ER and PR positive) (CRO: Start).

FIG. 7. Antitumor activity of SYD985 compared to T-DM1 in GXA3057 PDX model (gastric cancer, HER2 IHC 1+, HER2 FISH negative) (CRO: Oncotest).

FIG. 8. Antitumor activity of SYD985 compared to T-DM1 in GXA3067 PDX model (gastric cancer, HER2 IHC 2+, HER2 FISH positive) (CRO: Oncotest).

FIG. 9. Antitumor activity of SYD985 compared to T-DM1 in GXA3054 PDX model (gastric cancer, HER2 IHC 3+, HER2 FISH positive) (CRO: Oncotest).

FIG. 10. Antitumor activity of SYD985 compared to T-DM1 in GXA3038 PDX model (gastric cancer, HER2 IHC 2+, HER2 FISH negative) (CRO: Oncotest).

FIG. 11. Antitumor activity of SYD985 in BXF439 PDX model (bladder cancer, HER2 IHC 3+, HER2 FISH positive) (CRO: Oncotest).

FIG. 12. Antitumor activity of SYD983 in SKOV3 cell line-derived xenograft model (ovarian cancer, HER2 IHC 2+, HER2 FISH positive) (CRO: Piedmont).

DETAILED DESCRIPTION OF THE PRESENT INVENTION

The present invention relates to duocarmycin-containing ADCs for use in the treatment of human solid tumours and haematological malignancies expressing HER2.

In one embodiment, the present invention provides a compound of formula (I)

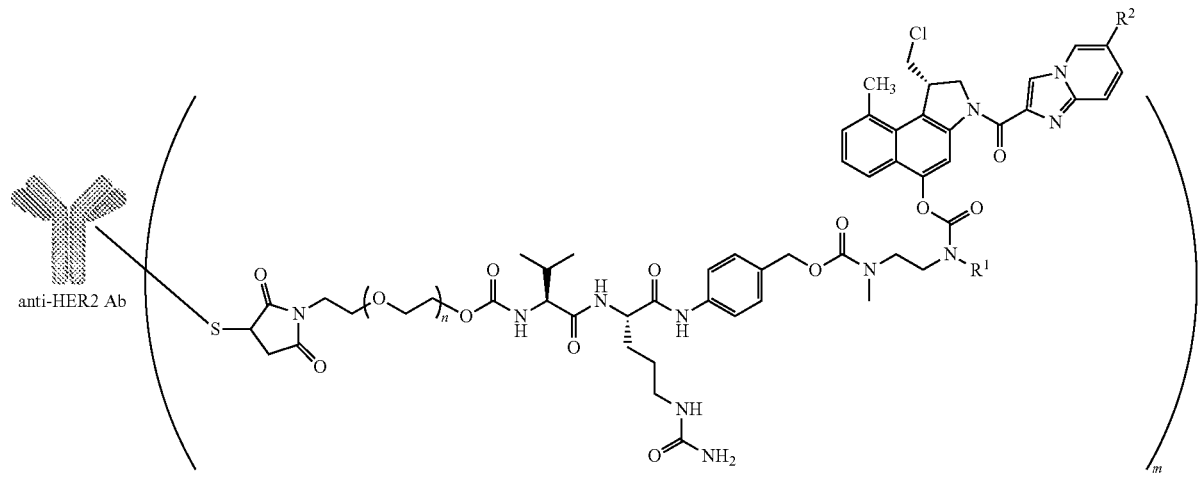

wherein anti-HER2 Ab is an anti-HER2 antibody or antibody fragment, n is 0-3, preferably 0-1, m represents an average DAR (drug-to-antibody ratio) of from 1 to 4, $R^1$ is selected from

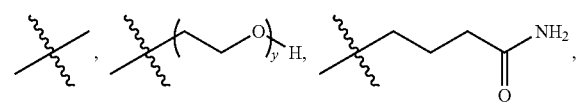

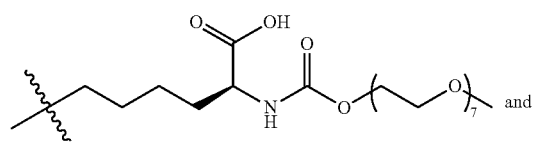

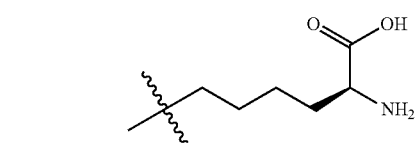

y is 1-16, and $R^2$ is selected from

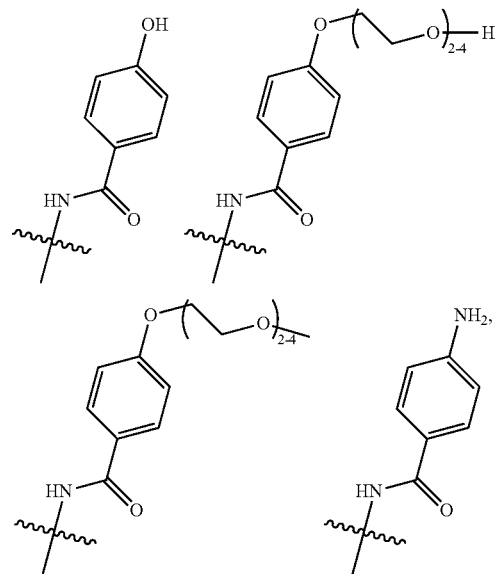

for use in the treatment of human solid tumours and haematological malignancies expressing HER2, in particular for use in the treatment of human solid tumours.

In another embodiment, the present invention relates to a compound of formula (I), wherein anti-HER2 Ab is an anti-HER2 antibody or antibody fragment, n is 0-1, m represents an average DAR of from 1 to 4, preferably from 2 to 3, $R^1$ is selected from

-continued

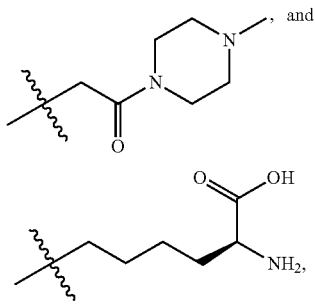

y is 1-16, preferably 1-4, and R² is selected from

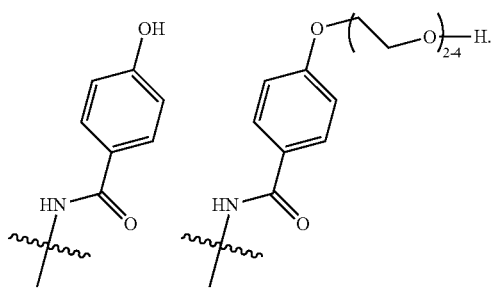

In a further embodiment, the present invention relates to a compound of formula (I), wherein the anti-HER2 Ab is an anti-HER2 monoclonal antibody, n is 0-1, m represents an average DAR of from 2 to 3, preferably from 2.5 to 2.9, R¹ is selected from

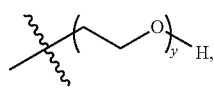

y is 1-4, and R² is selected from

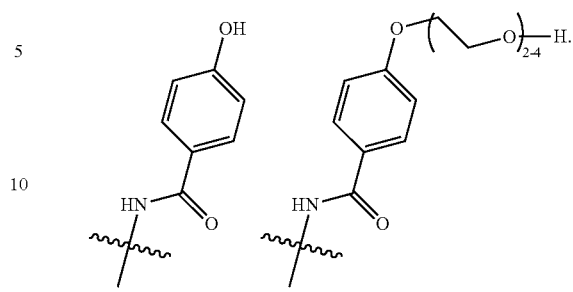

In yet another embodiment, the present invention relates to a compound of formula (I), wherein the anti-HER2 Ab is trastuzumab or a biosimilar thereof, n is 0-1, m represents an average DAR of from 2 to 3, preferably 2.5 to 2.9, R¹ is selected from

y is 1-4, and R² is selected from

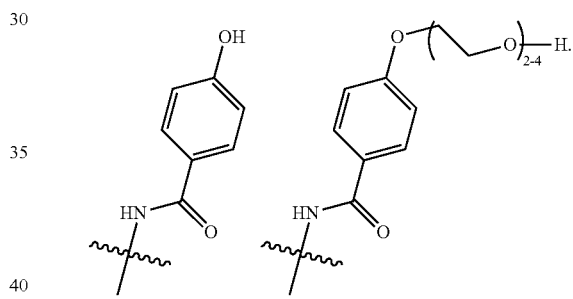

In a preferred embodiment, the present invention relates to a compound of formula (II), comprising trastuzumab or a biosimilar thereof

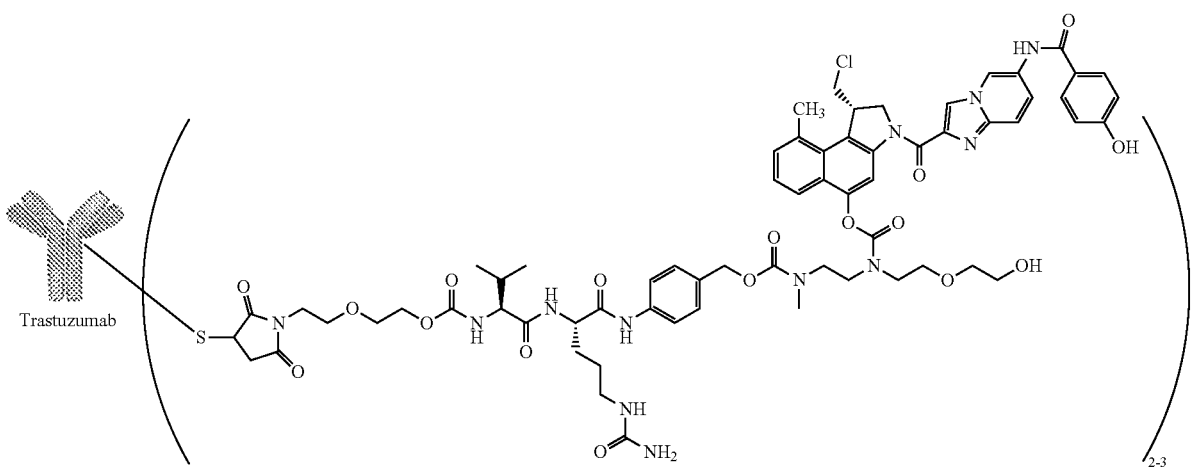

The compound of formula (II) that is referred to as SYD985 in the present specification has an average DAR of from 2.6 to 2.9. SYD983 of formula (II) has an average DAR of 2.0.

In the structural formulae shown in the present specification, n represent an integer from 0 to 3, while m represents an average drug-to-antibody ratio (DAR) of from 1 to 4. As is well-known in the art, the DAR and drug load distribution can be determined, for example, by using hydrophobic interaction chromatography (HIC) or reversed phase high-performance liquid chromatography (RP-HPLC). HIC is particularly suitable for determining the average DAR.

Examples of human solid tumours which can be treated in accordance with the present invention are breast cancer, gastric cancer, bladder cancer, ovarian cancer, lung cancer, prostate cancer, pancreatic cancer, colorectal cancer, head and neck squamous cell cancer, and osteosarcoma, particularly breast cancer, gastric cancer, bladder cancer, ovarian cancer, lung cancer, and prostate cancer, more particularly breast cancer, gastric cancer, and bladder cancer (see also S. Scholl et al., 2001, Ann. Oncol., 12(1): S81-S87). An example of a haematological malignancy which can be treated in accordance with the present invention is acute lymphoblastic leukaemia (ALL). The scope of the present invention however is not restricted to these specific examples.

In one embodiment, the present invention provides a compound of formula (I) or (II) for use in the treatment of breast cancer, gastric cancer or bladder cancer, particularly breast cancer or gastric cancer, especially breast cancer. Said breast cancer either is hormone receptor (ER and/or PR) positive or negative, advantageously ER and PR negative.

In another embodiment, the present invention provides a compound of formula (I) or (II) for use in the treatment of human solid tumours showing moderate or low expression of HER2 (i.e. HER2 IHC 2+ or 1+).

In yet another embodiment, the present invention provides a compound of formula (I) or (II) for use in the treatment of human solid tumours without HER2 gene amplification (i.e. HER2 FISH negative).

Unexpectedly, the present inventors have found that the duocarmycin-containing ADC compounds of the present invention particularly can be used for the treatment of human solid tumours, especially breast cancer and gastric cancer, with a moderate or low expression of HER2 (i.e. HER2 IHC 2+ or 1+) and/or without HER2 gene amplification (i.e. HER2 FISH negative). Neither trastuzumab nor T-DM1 obtained marketing approval for the treatment of patients having such tumours. Furthermore, as shown in the Examples and Figures herein below, T-DM1 lacks efficacy in such tumours. Hence, the duocarmycin-containing ADC compounds of the present invention can be used for the treatment of patient groups for which there is no current HER2-targeted therapy available. The duocarmycin-containing ADC compounds that were tested in mice bearing an N87 (i.e. HER2 IHC 3+ gastric tumour) xenograft in Example 15 of WO2011/133039A indeed showed efficacy after a single i.v. dose of 12 mg/kg. However, there is nothing in this document suggesting the person skilled in the art to test—let alone expect to find efficacy—in lower grade HER2-expressing tumours (i.e. HER2 IHC 2+ or 1+) and/or without HER2 gene amplification (i.e. HER2 FISH negative), already at a dose of 3 mg/kg.

The present inventors surprisingly further found that the duocarmycin-containing ADC compounds of formula (I) or (II) show an improved in vivo antitumor activity in animal tumour models as compared to T-DM1 (see Examples and Figures) and trastuzumab when administered at the same dose. Notably, it was found that the improvement was the highest in tumour models with the lowest grade of HER2 expression (i.e. IHC HER2 1+), in particular in (triple negative) breast cancer and gastric cancer.

In an advantageous embodiment of the present invention the human solid tumour is breast cancer or gastric cancer showing moderate or low HER2 expression (i.e. HER2 IHC 2+ or 1+) without HER2 gene amplification (i.e. HER2 FISH negative).

In a particularly advantageous embodiment of the present invention, the human solid tumour is triple negative breast cancer (i.e. HER2 IHC 2+ or 1+, HER2 FISH negative, and ER and PR negative).

Typically, the antitumor activity is evaluated first in (human) tumour cell lines in vitro followed by evaluation in vivo. The antitumor activity of the ADCs falling within the scope of the present invention advantageously is evaluated in animal models, typically immunodeficient mice bearing a subcutaneous xenograft. The xenograft can either be a (human) tumour cell line or a patient-derived (primary) tumour. Preferably, the animal model is a patient-derived tumour xenograft (PDX) model.

Human tumours in PDX models retain the biological characteristics of the original tumour as assessed by microscopic examination. PDX models are routinely used now in many academic institutions and are offered commercially by a number of Contract Research Organizations (CROs) including Jackson Lab (USA), Oncotest (Germany), Molecular Response (USA), Charles River (USA), Oncodesign (France), XenTech (France), Champions Oncology (USA), and Start (USA). Many have shown the retention of characteristic morphologic and immunohistochemical features of the original human tumour in the xenograft. Besides the close relationship with regards to biological characteristics, PDX models have a very good predictive value for therapeutic clinical outcome. In general, one could state that reports from different sources indicate at least 90% correct replication of the response to therapy in the PDX compared to that in the patient, both in terms of sensitivity and resistance of the tumour to therapy (Website Champions Oncology, http://www.championsoncology.com/translational-oncology-solutions/predictive-value; Fiebig et al., 1984, Behring Inst. Mitt. 74:343-352; Hidalgo et al., 2011, Mol. Cancer Ther. 10:1311-1316).

In accordance with the present invention, the anti-HER2 antibody or antibody fragment can be any antibody or antibody fragment able to bind HER2, e.g. an IgG1 antibody having the complementary determining regions (CDRs) of trastuzumab or an antibody that shows competitive binding with trastuzumab. A preferred antibody is a monoclonal anti-HER2 antibody. A particularly preferred monoclonal antibody is trastuzumab or a biosimilar thereof.

Antibody-drug conjugate (ADC) compounds of formula (I) and (II) in accordance with the present invention have the linker-drug conjugated to the antibody through the S-atom of a cysteine residue, i.e. they are cysteine-linked antibody-drug conjugates. The cysteine residue can either be a natural cysteine residue which is present in the heavy and/or light chain of the antibody (Ab) and forms inter-chain disulfide bonds, or an engineered cysteine residue which is introduced into the Ab at one or more suitable positions in the heavy and/or light chain. The present invention is particularly drawn to ADC compounds wherein the linker-drug is conjugated through inter-chain disulfide bonds of Abs, more particularly monoclonal Abs (mAbs). Antibodies of different antibody classes contain different numbers of interchain disulfide bonds. For example, IgG1 antibodies typically have four inter-chain disulfide bonds, all four located in the hinge region, and after (partial) reduction of the disulfide bonds the linker-drug is randomly attached to free thiol groups.

Compounds of formula (I) and (II) for use in accordance with the present invention can be obtained according to methods and procedures that are well known to a person skilled in the art. Conjugation through inter-chain disulfide bonds can occur after complete or partial reduction of said disulfide bonds. Suitable methods for preparing such compounds can be found in the description and examples of Applicant's WO2011/133039A. In particular, Example 15 of WO2011/133039A describes the partial reduction of trastuzumab to generate 2 free thiol groups per mAb and conjugation with a number of linker-drugs to ADCs having an average DAR of approx. 2. It is easily understood by those skilled in the art how to obtain ADCs having an average DAR of from 1 to 4. Examples 7 and 8 of WO2005/084390A describe partial reduction, partial reduction/partial re-oxidation, and complete reduction strategies for (partial) loading of antibodies with the linker-drug vcMMAE.

IHC and FISH status of the tumour tissue are determined using known tests, procedures and equipment. In accordance with the present invention HER2 gene amplification can be measured using either fluorescence (FISH) or chromogenic (CISH) or any other in situ hybridization test. Suitable tests for determination of the HER2 membrane expression status of the tumour tissue like the HercepTest™ (Dako Denmark) are commercially available. Further HER2 IHC tests are marketed by Ventana Medical Systems (PATHWAY anti-HER2/neu), Biogenex Laboratories (InSite™ HER2/neu), and Leica Biosystems (Bond Oracle™ HER2 IHC). FISH/CISH tests can be obtained from Abbott Molecular (PathVysion HER2 DNA Probe Kit), Life Technologies (SPOT-Light® HER2 CISH Kit), Dako Denmark (HER2 CISH PharmDx™ Kit), Dako Denmark (HER2 FISH PharmDx™ Kit), and Ventana Medical Systems (INFORM HER2 Dual ISH DNA Probe Cocktail). FISH positive means a FISH amplification ratio ≥2.0 (e.g. by using Dako HER2 FISH PharmDX™ test kit). FISH negative means a FISH amplification ratio <2.0.

HER2 expressing tumours which can be advantageously treated in accordance with the present invention are breast cancer and gastric cancer, particularly breast cancer, most particularly triple negative breast cancer. Unexpectedly, the present inventors have found that the ADC compounds in accordance with the present invention notably were effective in breast cancer PDX models which are HER2 IHC 2+ or 1+ and FISH negative, in triple negative breast cancer PDX models, and in gastric cancer PDX models which are HER2 IHC 2+ or 1+ and FISH negative, as shown in the Examples and Figures herein below. In view of the fact that PDX models have a very good predictive value for therapeutic clinical outcome, these findings particularly offer a new HER2-targeted treatment option for breast and gastric cancers for which there is currently no such approved treatment option available.

The present invention also relates to the use of a compound of formula (I) or (II) for the treatment of patients having human solid tumours or haematological malignancies expressing HER2, in particular of human solid tumours which are HER2 IHC 2+ or 1+ and/or which are HER2 FISH negative as described herein above.

The present invention further relates to the use of a combination of a compound of formula (I) or (II) with a therapeutic antibody and/or a chemotherapeutic agent, for the treatment of human solid tumours and haematological malignancies expressing HER2, in particular human solid tumours, most particularly for the treatment of triple negative breast cancer.

In one embodiment of the present invention, the therapeutic antibody is pertuzumab, bevacizumab, ramucirumab or trastuzumab and the chemotherapeutic agent is i) a taxane, particularly docetaxel, paclitaxel, nab-paclitaxel, or cabazitaxel, ii) a mitotic inhibitor, particularly eribulin, vinorelbine or vinblastine, iii) a DNA damaging agent, particularly 5-fluoro-uracil, capecitabine, gemcitabine, temozolomide, cisplatin, carboplatin, oxaliplain, cyclophosphamide or ifosfamide, iv) an anti-folate, particularly pemetrexed or methotrexate, v) an anthracycline, particularly mitoxantrone, doxorubicin, liposomal doxorubicin, epirubicin, daunorubicin or valrubicin, more particularly doxorubicin, vi) an mTOR (mammalian target of rapamycin) inhibitor, particularly temsirolimus or everolimus, vii) a topo-isomerase inhibitor, particularly irinotecan or topotecan, viii) a tyrosine kinase inhibitor, particularly gefitinib, erlotinib, pazopanib, crizotinib, lapatinib or afatinib, ix) an androgen receptor modulating agent, particularly enzalutamide or abiraterone acetate, x) a steroid hormone, particularly prednisone, xi) a hormonal therapeutic agent, particularly tamoxifen, xii) an aromatase inhibiting or steroid modifying agent, particularly anastrozole, letrozole, fulvestrant or exemestane, or xiii) a PARP inhibitor, particularly olaparib. The person skilled in the art will have no difficulty in selecting suitable combination therapies for use in the treatment of human solid tumours and haematological malignancies expressing HER2.

In another embodiment of the present invention, the therapeutic antibody is pertuzumab and the chemotherapeutic agent is a taxane, particularly docetaxel or paclitaxel, or an anthracycline, particularly doxorubicin, epirubicin, daunorubicin or valrubicin, more particularly doxorubicin.

The present invention further relates to the use of a combination of a compound of formula (I) or (II) with another ADC, such as for example T-DM1, for the treatment of human solid tumours and haematological malignancies expressing HER2, in particular human solid tumours expressing HER2.

The present invention further relates to a pharmaceutical composition comprising a compound of formula (I) or (II) or a combination with a therapeutic antibody and/or a chemotherapeutic agent thereof as described herein above, and one or more pharmaceutically acceptable excipients.

Typical pharmaceutical formulations of therapeutic proteins such as monoclonal antibodies and (monoclonal) antibody-drug conjugates take the form of lyophilized powders or cakes, which require (aqueous) dissolution (i.e. reconstitution) before intravenous infusion, or frozen (aqueous) solutions, which require thawing before use. Particularly, in accordance with the present invention the pharmaceutical composition is provided in the form of a lyophilized cake.

Suitable pharmaceutically acceptable excipients for inclusion into the pharmaceutical composition (before freeze-drying) in accordance with the present invention include buffer solutions (e.g. citrate, histidine or succinate containing salts in water), lyo protectants (e.g. sucrose, trehalose), tonicity modifiers (e.g. sodium chloride), surfactants (e.g. polysorbate), and bulking agents (e.g. mannitol, glycine). Excipients used for freeze-dried protein formulations are selected for their ability to prevent protein denaturation during the freeze-drying process as well as during storage.

The sterile, lyophilized powder multi-dose formulation of Herceptin™ contains 440 mg trastuzumab, 400 mg α,α- trehalose dihydrate, 9.9 mg L-histidine.HCl, 6.4 mg L-histidine, and 1.8 mg polysorbate 20, USP. Reconstitution with 20 ml of Bacteriostatic or Sterile Water for Injection (BWFI or SWFI) yields a multi-dose solution containing 21 mg/ml trastuzumab at a pH of approximately 6. The sterile, lyophilized powder single-use formulation of Kadcyla™ contains upon reconstitution 20 mg/ml ado-trastuzumab emtansine, 0.02% w/v polysorbate 20, 10 mM sodium succinate, and 6% w/v sucrose with a pH of 5.0.

A therapeutically effective amount of the compound of formula (I) or (II) for use in accordance with the present invention lies in the range of about 0.01 to about 15 mg/kg body weight, particularly in the range of about 0.1 to about 10 mg/kg, more particularly in the range of about 0.3 to about 10 mg/kg body weight. This latter range corresponds roughly to a flat dose in the range of 20 to 800 mg of the ADC compound. The compound of the present invention is administered weekly, bi-weekly, three-weekly or monthly, for example weekly for the first 12 weeks and then every three weeks until disease progression. Alternative treatment regimens may be used depending upon the severity of the disease, the age of the patient, the compound being administered, and such other factors as would be considered appropriate by the treating physician.

EXAMPLES

PDX HER2 Gene Amplification Testing

Amplification of the HER2 gene was determined by in situ hybridization (ISH) in formalin-fixed, paraffin-embedded human breast cancer tissue specimens using FDA approved tests from Ventana Medical Systems (INFORM HER2 Dual ISH DNA Probe Cocktail) or Abbott Molecular (PathVysion HER2 DNA Probe Kit). Protocols used were as detailed by the suppliers of the tests.

PDX HER2 IHC Staining

Tissue sections of formalin-fixed, paraffin-embedded tumour xenograft samples were prepared. HER2 was bound by using a suitable Ab, for instance a polyclonal rabbit anti-human HER2 (DAKO Cat #A0485) antibody and detected by a suitable secondary Ab, for instance biotinylated goat anti-rabbit IgG (JacksonImmuno research, Cat #111-065-04) and a Biozol (Cat #VEC-PK-4000) ABC kit. Staining was evaluated semi-quantitatively on a suitable microscope, for instance using a Zeiss Axiovert 35 microscope. Staining was interpreted as immunoreactivity, based on the number of stained tumour cells as well as the completeness and intensity of the membrane staining.

0: <10% of the tumour cells exhibit membranous stain.

1: >10% of the tumour cells exhibit membranous stain, but incomplete stain of surface.

2: >10% of the tumour cells exhibit weak or moderate membranous stain distributed all over the surface.

3: >30% of the tumour cells exhibit strong membranous stain distributed all over the surface.

Known HER2 positive (IHC 3+) and HER2 negative (IHC 0) control tumour slides were included in every HER2 staining procedure.

PDX and cell line-derived xenograft animal studies All animal studies were approved by local animal ethical committees and were performed according to local ethical guidelines of animal experimentation. Female immunodeficient nu/nu mice (4-6 weeks of age) or SCID mice from a professional animal breeder like Harlan or Charles River were used and randomization was performed according to the detailed protocols of the respective CROs, as described for instance by Fiebig et al. in Cancer Genomics & Proteomics 4: 197-210, 1997.

All breast and gastric PDX studies were performed testing SYD985 head-to-head to T-DM1, since the latter ADC was approved for treatment of patients with HER2-positive metastatic breast cancer and approval for T-DM1 in HER2-positive gastric cancer is currently being pursued. Studies in other indications (bladder and ovarian) were done using SYD985 only, since T-DM1 is not an approved drug in those indications. Mice were treated with either vehicle, 3 mg/kg SYD985 or 3 mg/kg T-DM1 in all breast PDX models (FIGS. 1-6) and with vehicle, 10 mg/kg SYD985 or 10 mg/kg T-DM1 in all gastric PDX models (FIGS. 7-10). Mice were treated with vehicle or 10 mg/kg SYD985 in the bladder PDX model (FIG. 11) and with vehicle or 15 mg/kg SYD983 in the cell line-derived ovarian xenograft model (FIG. 12). All treatments were conducted at day 0 by a single dose, i.v. injection into the tail vein. Data, depicted as mean tumour volume±S.D., consists of 6-8 animals per experimental group. Body weight and tumour size were measured twice weekly. The tumour volume was determined by a two-dimensional measurement with callipers. Termination criteria included among others a tumour volume >2000 mm$^3$ or a body weight loss >30%. Tumour size of individual animals was processed using GraphPad Prism. The results are shown in FIGS. 1 to 12.

First-in-Human Clinical Study

A two-part first-in-human phase I study (with expanded cohorts) with the antibody-drug conjugate SYD985 (trastuzumab vc-seco-DUBA) is being performed to evaluate the safety, pharmacokinetics and efficacy in patients with locally advanced or metastatic solid tumours (i.e. NCT02277717). Part I is the dose-escalation part in which a low dose of SYD985 is given to three cancer patients (females or males having solid tumours of any origin). If it is well tolerated, a higher dose of SYD985 will be given to three other cancer patients. This will continue until it is not safe anymore to increase the dose further. In part II of the study, several groups of patients with a specific type of cancer (including breast and gastric tumours) will receive the SYD985 dose selected for further development. All patients from both parts of the study (it is estimated that a total of 76 patients will be enrolled) will receive SYD985 (intravenous) infusions every three weeks until progression of the cancer or unacceptable toxicity develops.

The invention claimed is:

1. A method of treating bladder cancer in a human patient, comprising administering to the patient a therapeutically effective amount of a compound of formula (I)

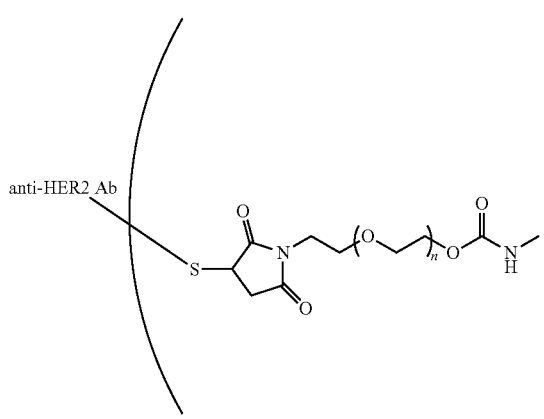

-continued

[Structure: valine-citrulline-p-ethylaniline dipeptide]

[Structure: drug moiety with chloromethyl, methyl, naphthalene-fused indoline, imidazopyridine with R², carbamate linker to N-R¹, with subscript m]

wherein
anti-HER2 Ab is an anti-HER2 antibody or antibody fragment able to bind HER2,
n is 0, 1, 2, or 3,
m represents an average DAR of from 1 to 4,
R¹ is selected from the group consisting of

[Structures for R¹: methyl/branch, PEG chain —(OCH₂CH₂)$_y$—H, —(CH₂)₃C(O)NH₂, N-methylpiperazine acetyl, lysine-PEG₇-carbamate, and lysine]

y is 1-16, and
R² is selected from the group consisting of

[Structures for R²: 4-hydroxyphenyl benzamide, 4-PEG₂₋₄-phenyl benzamide, another PEG-phenyl benzamide, and 4-aminophenyl benzamide]

and
wherein the patient has HER2 positive bladder cancer.

2. The method according to claim 1, wherein
n is 0 or 1,
R¹ is selected from the group consisting of

[Structures: methyl branch, PEG —(OCH₂CH₂)$_y$—H, N-methylpiperazine acetyl, and lysine]

and
R² is

[Structures: 4-hydroxyphenyl benzamide or 4-PEG₂₋₄-phenyl benzamide]

3. The method according to claim 2, wherein
anti-HER2 Ab is an anti-HER2 monoclonal antibody,
m represents an average DAR of from 2 to 3,
$R^1$ is

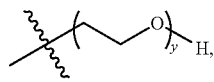

and
y is 1, 2, 3, or 4.

4. The method according to claim 1, wherein said bladder cancer is IHC 3+.

5. The method according to claim 1, wherein said anti-HER2 Ab is trastuzumab.

6. The method according to claim 1, wherein the compound of formula (I) is a compound of formula (II)

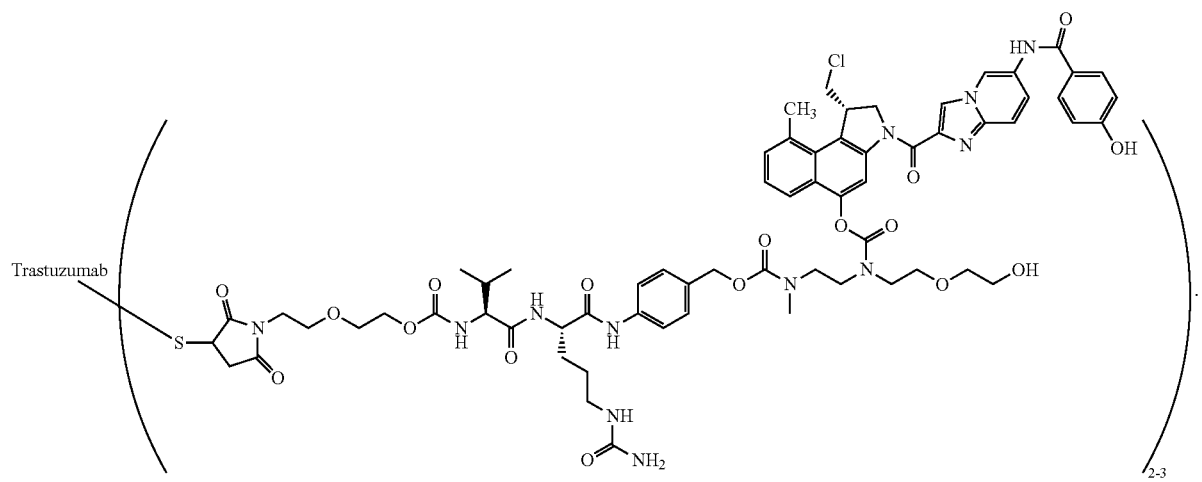

7. The method according to claim 6, wherein the compound of formula (II) has an average DAR of from 2.5 to 2.9.

8. The method according to claim 6, wherein the compound of formula (II) has an average DAR of from 2.6 to 2.9.

9. The method according to claim 1, further comprising administering an effective amount of a therapeutic antibody or a chemotherapeutic agent, or a combination thereof.

10. The method according to claim 9, wherein the therapeutic antibody is pertuzumab and the chemotherapeutic agent is a taxane or an anthracycline.

* * * * *